US011484287B2

(12) United States Patent
Zwierstra et al.

(10) Patent No.: US 11,484,287 B2
(45) Date of Patent: Nov. 1, 2022

(54) SYSTEMS AND METHODS FOR MODULAR HEADSET SYSTEM

(71) Applicant: NovaSignal Corp., Los Angeles, CA (US)

(72) Inventors: Jan Zwierstra, Los Angeles, CA (US); Kiah Lesher, Los Angeles, CA (US); Matthew Hutter, Los Angeles, CA (US); Lane Stith, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 0 days.

(21) Appl. No.: 16/789,341

(22) Filed: Feb. 12, 2020

(65) Prior Publication Data

US 2020/0261055 A1    Aug. 20, 2020

Related U.S. Application Data

(60) Provisional application No. 62/805,839, filed on Feb. 14, 2019.

(51) Int. Cl.
*A61B 8/00* (2006.01)
*A61B 5/00* (2006.01)
(Continued)

(52) U.S. Cl.
CPC .......... *A61B 8/4209* (2013.01); *A61B 5/0077* (2013.01); *A61B 5/70* (2013.01);
(Continued)

(58) Field of Classification Search
CPC ...... A61G 13/121; A42B 3/0473; A47C 7/38; A47C 7/383; A61B 90/14; A61B 8/4209;
(Continued)

(56) References Cited

U.S. PATENT DOCUMENTS 4,979,519 A * 12/1990 Chavarria ............ A61B 5/0555
128/857
6,648,416 B2 * 11/2003 O'Connor .............. A47C 7/383
297/397

(Continued)

FOREIGN PATENT DOCUMENTS

WO    WO-2017/143128 A1    8/2017
WO    WO-2019/055865 A1    3/2019

OTHER PUBLICATIONS

International Search Report and Written Opinion dated Aug. 10, 2020, from application No. PCT/US2020/017972.
(Continued)

*Primary Examiner* — Matthew A Eason
*Assistant Examiner* — Kuassi A Ganmavo
(74) *Attorney, Agent, or Firm* — Foley & Lardner LLP

(57) ABSTRACT

Arrangements described herein relate to systems, apparatuses, and methods for a headset system that includes a transducer configured to collect physiological data of a subject, a device housing configured to support the transducer, an insert portion disposed on the device housing, a support structure comprising a baseplate and a receiving portion, and a head cradle supported by the baseplate. The receiving portion extends in a direction that is oblique with respect to the baseplate. The insert portion is sized and shaped to engage the receiving portion to removably attach the device housing to the baseplate.

21 Claims, 22 Drawing Sheets

(51) Int. Cl.
   *A61B 8/08* (2006.01)
   *A61B 90/14* (2016.01)
   *A61N 2/00* (2006.01)
   *A61G 7/05* (2006.01)
   *H04R 1/10* (2006.01)
   *A61G 13/12* (2006.01)
   *A47C 7/38* (2006.01)
   *H04R 25/00* (2006.01)
   *A42B 3/04* (2006.01)

(52) U.S. Cl.
   CPC .......... *A61B 8/0808* (2013.01); *A42B 3/0473* (2013.01); *A47C 7/38* (2013.01); *A61B 8/488* (2013.01); *A61B 90/14* (2016.02); *A61G 7/05* (2013.01); *A61G 13/12* (2013.01); *A61N 2/006* (2013.01); *H04R 1/1008* (2013.01); *H04R 25/00* (2013.01)

(58) Field of Classification Search
   CPC ....... A61B 8/0816; A61B 5/0077; A61B 5/70; A61B 8/0808; A61B 8/488; H04R 1/1033; H04R 1/1008; H04R 25/00; A61N 2/006; A61N 2/02; A67F 5/37
   See application file for complete search history.

(56) References Cited

U.S. PATENT DOCUMENTS

| | | | | |
|---|---|---|---|---|
| 7,526,330 | B1* | 4/2009 | Randell | A61B 5/055 324/309 |
| 2005/0049486 | A1* | 3/2005 | Urquhart | A61B 34/20 600/429 |
| 2005/0121963 | A1* | 6/2005 | Williamson | B60N 2/18 297/408 |
| 2006/0081263 | A1* | 4/2006 | Ostrowski | A61F 5/05883 128/870 |
| 2007/0228792 | A1* | 10/2007 | Chen | B60N 2/2851 297/284.9 |
| 2010/0127541 | A1* | 5/2010 | Kotz | B60N 2/865 297/216.12 |
| 2011/0040174 | A1* | 2/2011 | Driemel | G01R 33/34007 600/422 |
| 2011/0218648 | A1* | 9/2011 | Younger | A61F 2/64 623/47 |
| 2015/0087924 | A1 | 3/2015 | Li et al. | |
| 2015/0238117 | A1* | 8/2015 | Fielder | A61G 13/121 5/637 |
| 2015/0297176 | A1* | 10/2015 | Rincker | A61B 8/429 600/439 |
| 2015/0300785 | A1* | 10/2015 | Lamparter | B60N 2/643 297/216.17 |
| 2016/0158082 | A1* | 6/2016 | Gainor | A61G 7/0524 5/690 |
| 2017/0014201 | A1* | 1/2017 | Grotenhuis | A61G 13/121 |
| 2017/0135492 | A1* | 5/2017 | Biancofiore | A47C 21/006 |
| 2017/0291037 | A1* | 10/2017 | Tamiya | A61N 2/02 |
| 2017/0311887 | A1 | 11/2017 | Leussler et al. | |
| 2017/0367651 | A1 | 12/2017 | Tzvieli et al. | |
| 2018/0085915 | A1* | 3/2018 | Hirose | F16D 27/112 |
| 2018/0214163 | A1* | 8/2018 | McCormick | A61B 17/8095 |
| 2019/0366027 | A1* | 12/2019 | Murray | A61G 13/121 |

OTHER PUBLICATIONS

Partial International Search Report dated Jun. 17, 2020, from application No. PCT/US2020/017972.
International Preliminary Report on Patentability dated Aug. 26, 2021, from application No. PCT/US2020/017972.

* cited by examiner

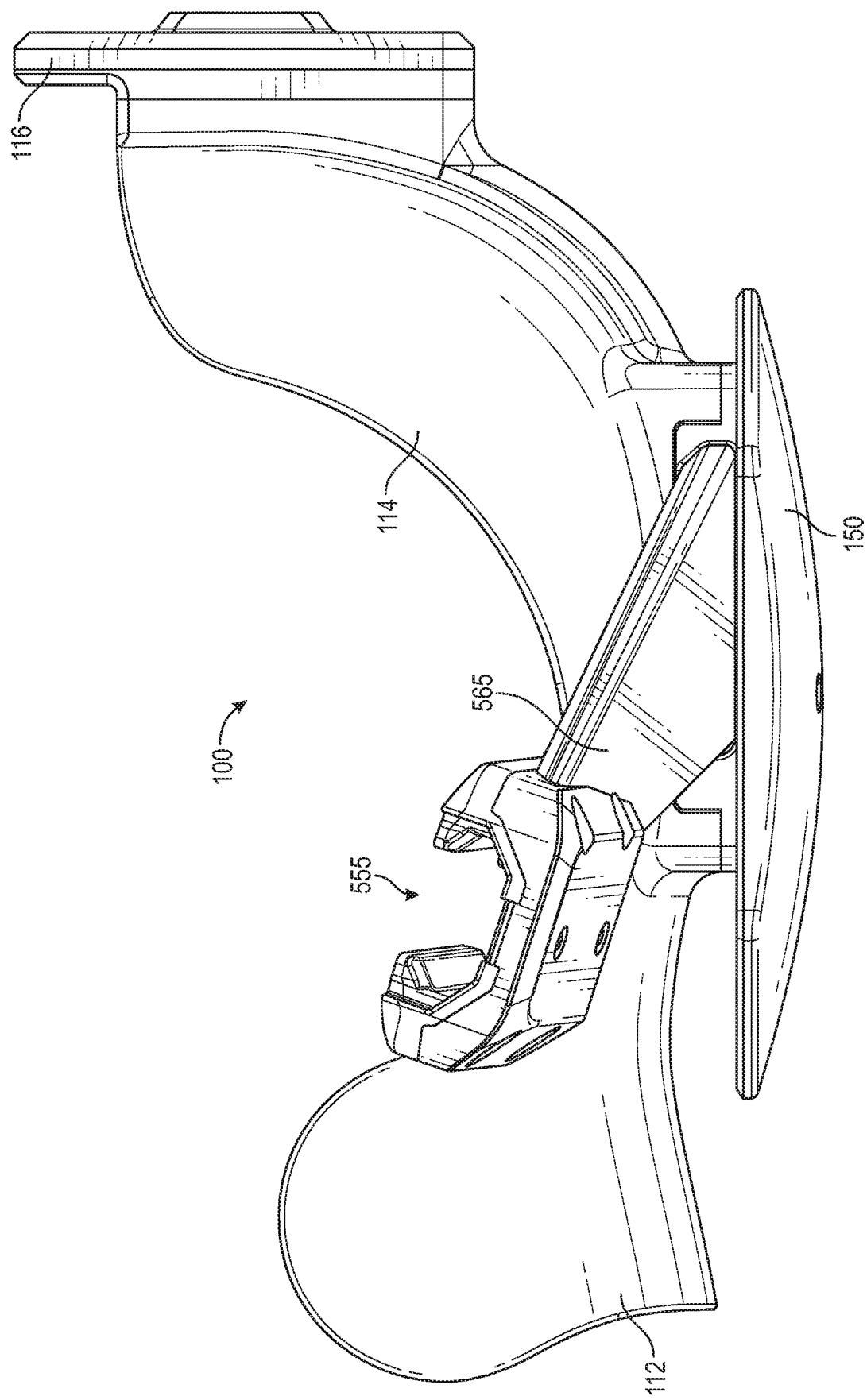

SYSTEMS AND METHODS FOR MODULAR HEADSET SYSTEM

CROSS-REFERENCE TO RELATED PATENT APPLICATIONS

This application claims priority from provisional U.S. Application No. 62/805,839, titled SYSTEMS AND METHODS FOR MODULAR HEADSET SYSTEM, filed Feb. 14, 2019, which is incorporated herein by reference in its entirety.

BACKGROUND

Performance of a device (e.g., optical devices, surgical devices, scanning devices, medical diagnostic devices, automated Transcranial Doppler devices, and so on) that is incorporated in a headset system is optimized based on the device's positioning with respect to a subject's head. Initial registration (e.g., alignment) of the device or an instrument (e.g., a probe) thereof with respect to particular areas of the subject's head is important for the device to operate effectively during its operation. In addition, a technician of the headset system performing manual registration of the device may introduce human errors such that performance of the device during operation can be adversely affected. Furthermore, a highly skilled technician is needed to properly register the device, and a lack of such highly skilled technician may impede efficient and timely administration of healthcare. These technical issues prevent such devices from being pervasive deployed.

SUMMARY

In some arrangements, a headset system includes a transducer configured to collect physiological data of a subject, a device housing configured to support the transducer, an insert portion disposed on the device housing, a support structure includes a baseplate and a receiving portion, and a head cradle supported by the baseplate. The receiving portion extends in a direction that is oblique with respect to the baseplate. The insert portion is sized and shaped to engage the receiving portion to removably attach the device housing to the baseplate.

In some arrangements, the receiving portion extends in an oblique direction from the baseplate.

In some arrangements, the receiving portion includes a body and a receptacle. The receptacle forms an aperture configured to receive the insert portion.

In some arrangements, the aperture has an inner surface includes slots. The insertion portion includes a rail having teeth. The teeth are sized and shaped to engage the slots when the insertion portion is engaged with the receiving portion.

In some arrangements, the insert portion includes an extension having a top surface and a bottom surface. The bottom surface faces away from the device housing. The rail is disposed on the bottom surface.

In some arrangements, the body extends in an oblique direction from the baseplate.

In some arrangements, the body extends from the baseplate in a first direction. The receptacle extends in a second direction. The first direction traverses the second direction.

In some arrangements, at least a portion of the insert portion has a flat shape.

In some arrangements, the device housing is configured to stand upright on a surface via the portion of the insert portion having the flat shape.

In some arrangements, the transducer extends from the device housing in a first direction. The insertion portion extends in a second direction. The first direction and the second direction are parallel.

In some arrangements, the headset system further includes an actuator configured to lock the insert portion in a position relative to the receiving portion when at least a part of the insert portion is inserted into the receiving portion.

In some arrangements, the actuator includes a latch disposed on the device housing.

In some arrangements, the insertion portion includes a rail having teeth. The actuator is configured to lock the insert portion in the position relative to the receiving portion by controlling a position of the rail.

In some arrangements, the actuator is configured to control the position of the rail via a lever mechanism connecting the actuator with the rail.

In some arrangements, the rail faces an opening slit of the receiving portion.

In some arrangements, the transducer extends from the device housing in a first direction. The actuator is arranged on a surface of the device housing that faces a second direction. The first direction and the second direction are opposite.

In some arrangements, the device housing includes a first portion and a second portion separate from the first portion. The first portion is configured to support the transducer. The actuator is disposed on the second portion.

In some arrangements, the insert portion is disposed on the first portion.

In some arrangements, the insert portion is disposed on the second portion.

In some arrangements, at least a portion of the insert portion is detachably mounted to the device housing.

In some arrangements, a headset system includes a transducer configured to collect physiological data of a subject, a device housing configured to support the transducer, the transducer is disposed on a front side of the device housing, an insert portion disposed on the device housing, a support structuring includes a baseplate and a receiving portion, a head cradle supported by the baseplate, and an actuator disposed on a back side of the device housing. The insert portion is sized and shaped to engage the receiving portion to removably attach the device housing to the baseplate. The front side and the back side are opposite sides of the device housing.

BRIEF DESCRIPTION OF THE FIGURES

Features, aspects, and advantages of the present disclosure will become apparent from the following description and the accompanying example arrangements shown in the drawings, which are briefly described below.

FIG. 3C illustrates a side view of the support structure of the headset system shown in FIG. 1 according to various arrangements.

DETAILED DESCRIPTION

Figure 1:
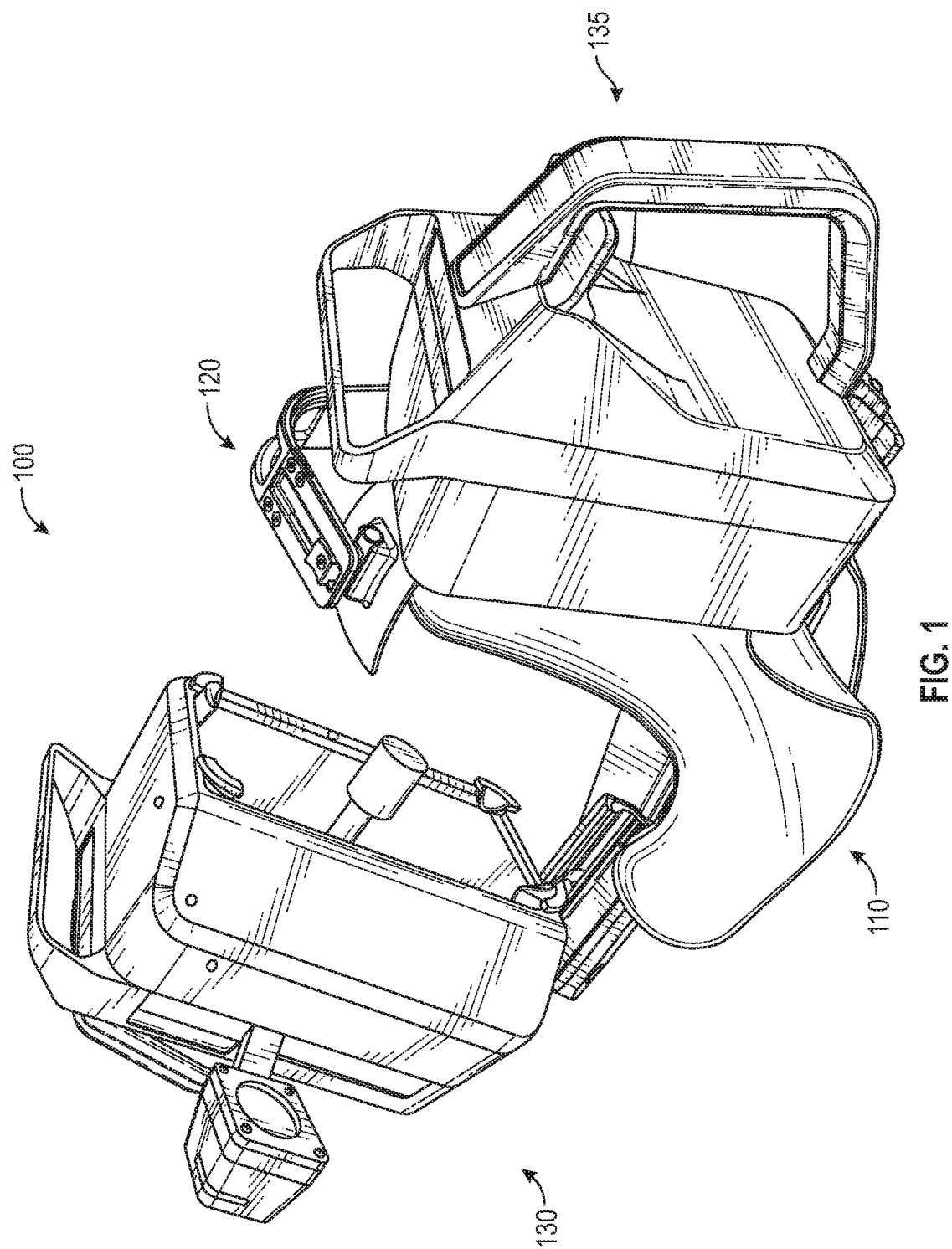
FIG. 1 illustrates a perspective view of a headset system according to various arrangements.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

The arrangements disclosed herein relate to systems, apparatuses, and methods for collecting physiological data (e.g., ultrasound data) of a portion (e.g., a head) of a subject. An example is a headset system, which includes a support structure (e.g., including a head cradle) configured to (sized and shaped to) support a portion (e.g., the head) of the subject and a device configured to collect the physiological data of the portion of the subject when that portion of the subject is supported by the support structure. The device includes a transducer (e.g., a probe) configured to collect the physiological data of the portion of the subject.

While the head of the subject is used as an example of the portion of the subject of which the device (e.g., the transducer) can collect the physiological data, the system can likewise collect physiological data of other body parts such as but not limited to, the limbs, the neck, the abdomen, the chest, the bones, various organs (e.g., the heart, the lungs, the liver, the skin, and so on), and so on. Similarly, while the head cradle is used as an example component of the support structure, the support structure can include any suitable structure or mechanism configured (e.g., shaped) to support and secure a corresponding portion of the subject while the device collects physiological data of that portion of the subject.

The device includes a device housing configured to support the transducer and robotics configured to move the transducer with respect to the subject to collect the physiological data. In that regard, the transducer is movably supported by the device housing. The device housing may further support a camera configured to register the transducer. The device can be detachably mounted to the support structure. The device housing includes at least one handle that enables the device to be carried by an operator and assembled with (e.g., attached to) the support structure. In that regard, the device and the support structure have suitable connection interfaces configured to allow the headset system to be assembled or dissembled by the operator without using of tools. As such, the device and the support structure can be transported and stored separately and can be assembled to perform the operations described herein. By providing the at least one handle, the operator can easily attach the device to or detach the device from the support structure.

FIG. 1 illustrates a perspective view of a headset system 100 according to various arrangements. Referring to FIG. 1, the headset system 100 is shown to include devices 130 and 135 that can be connected or attached to a support structure 110. The headset system 100 further includes a restraint system 120 configured to be connected or attached to the support structure 110.

Figure 2A:
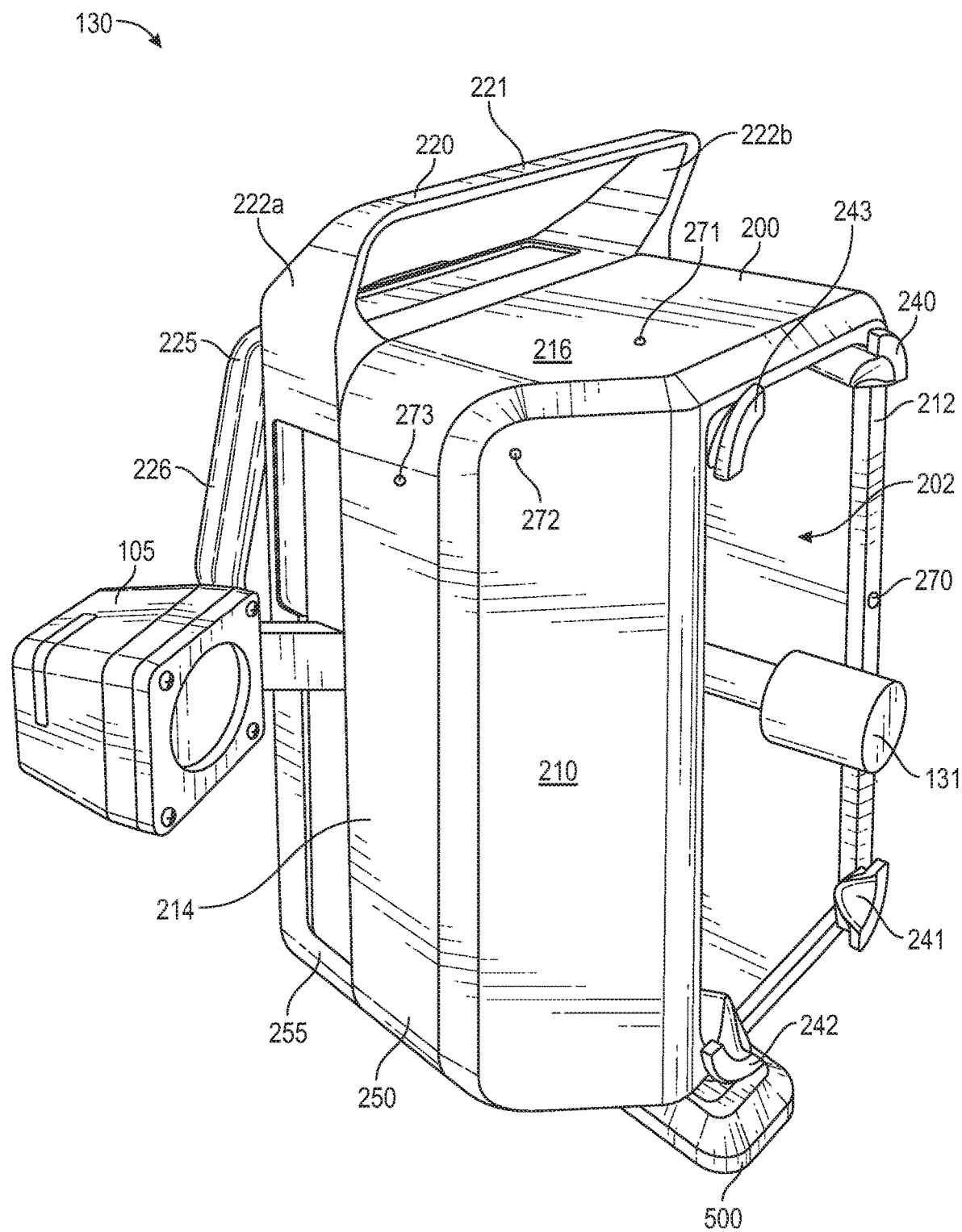
FIGS. 2A-2C illustrate perspective views of the device of the headset system shown in FIG. 1 according to various arrangements.
Figure 2B:
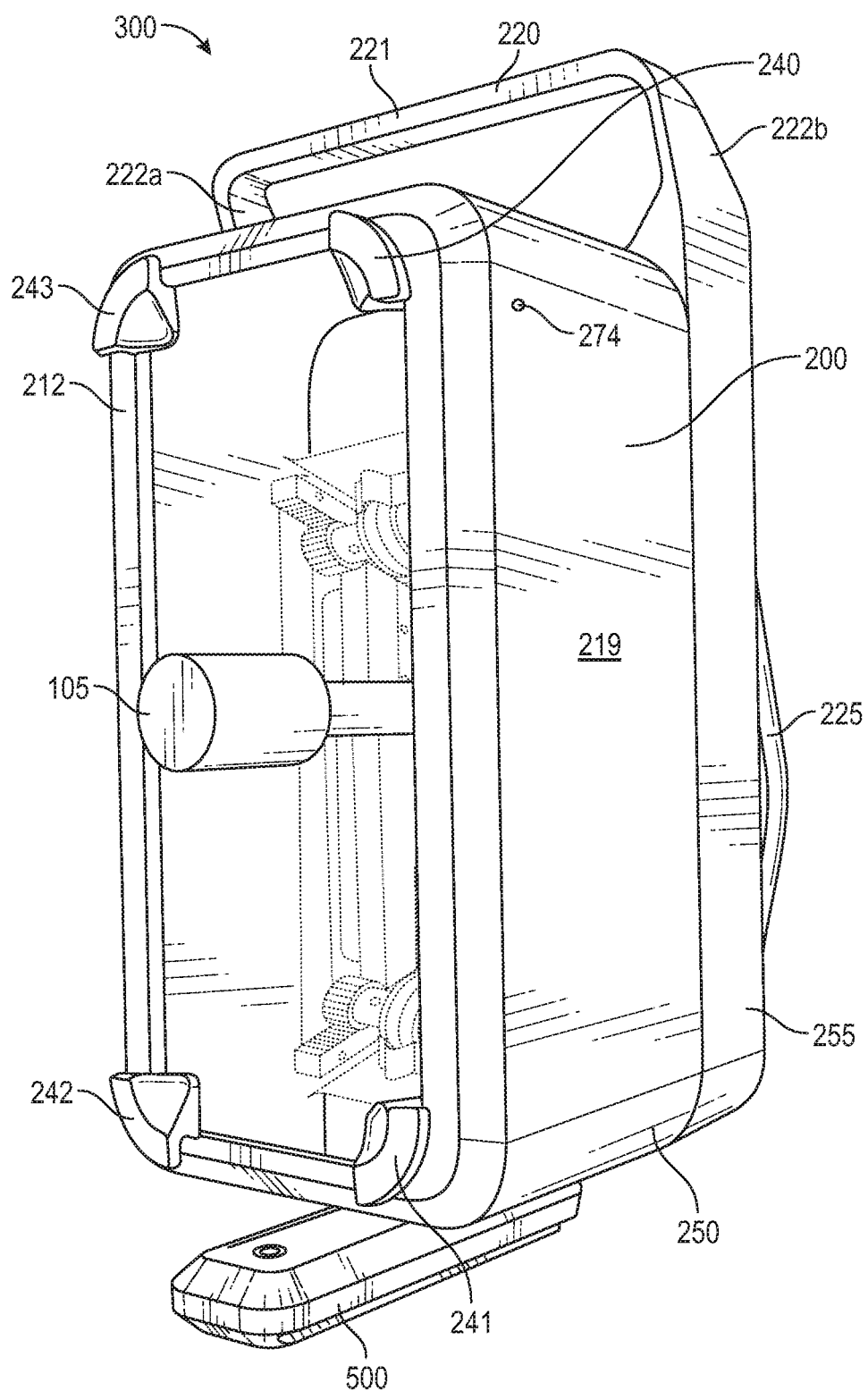
Figure 2C:
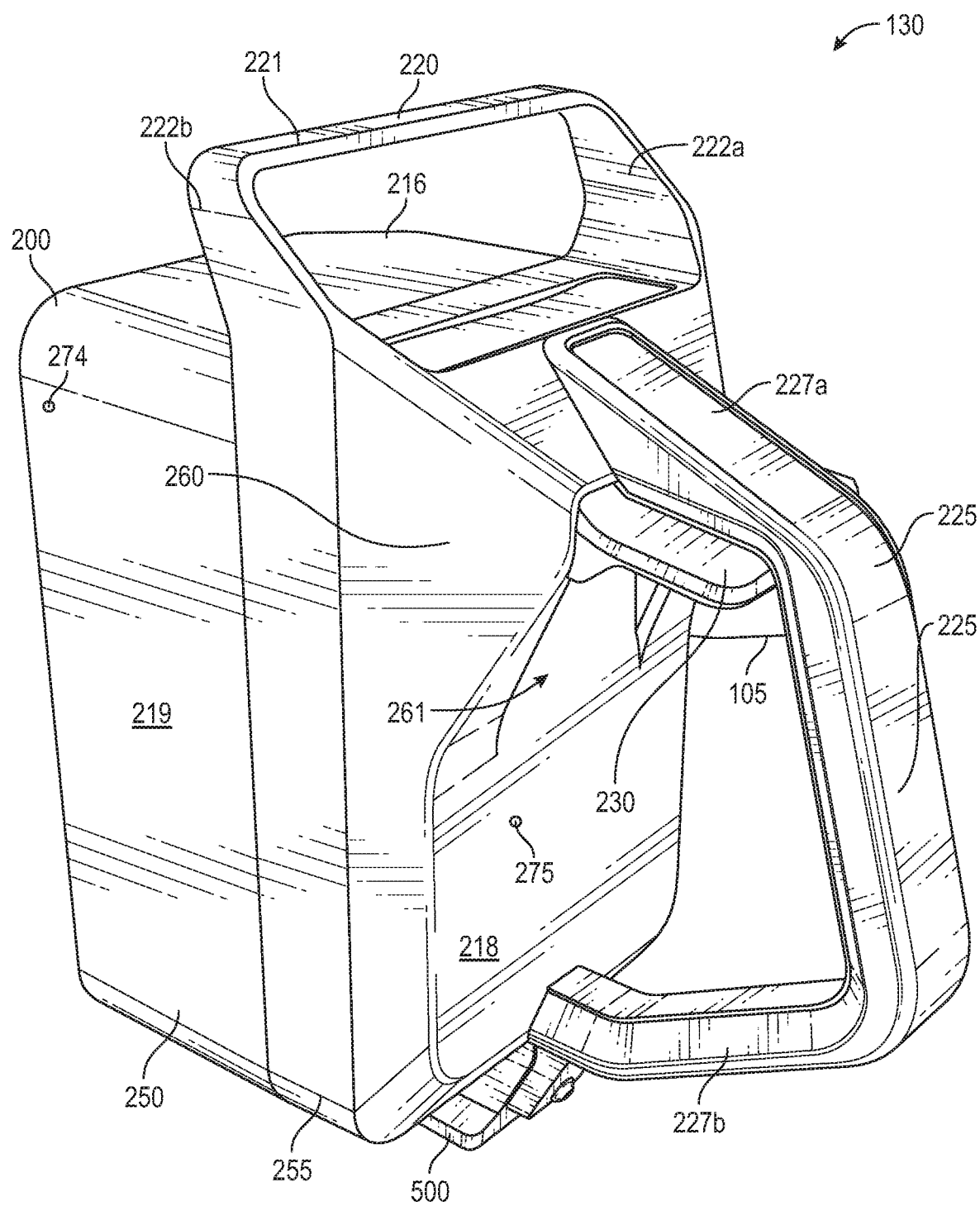
Figure 2D:
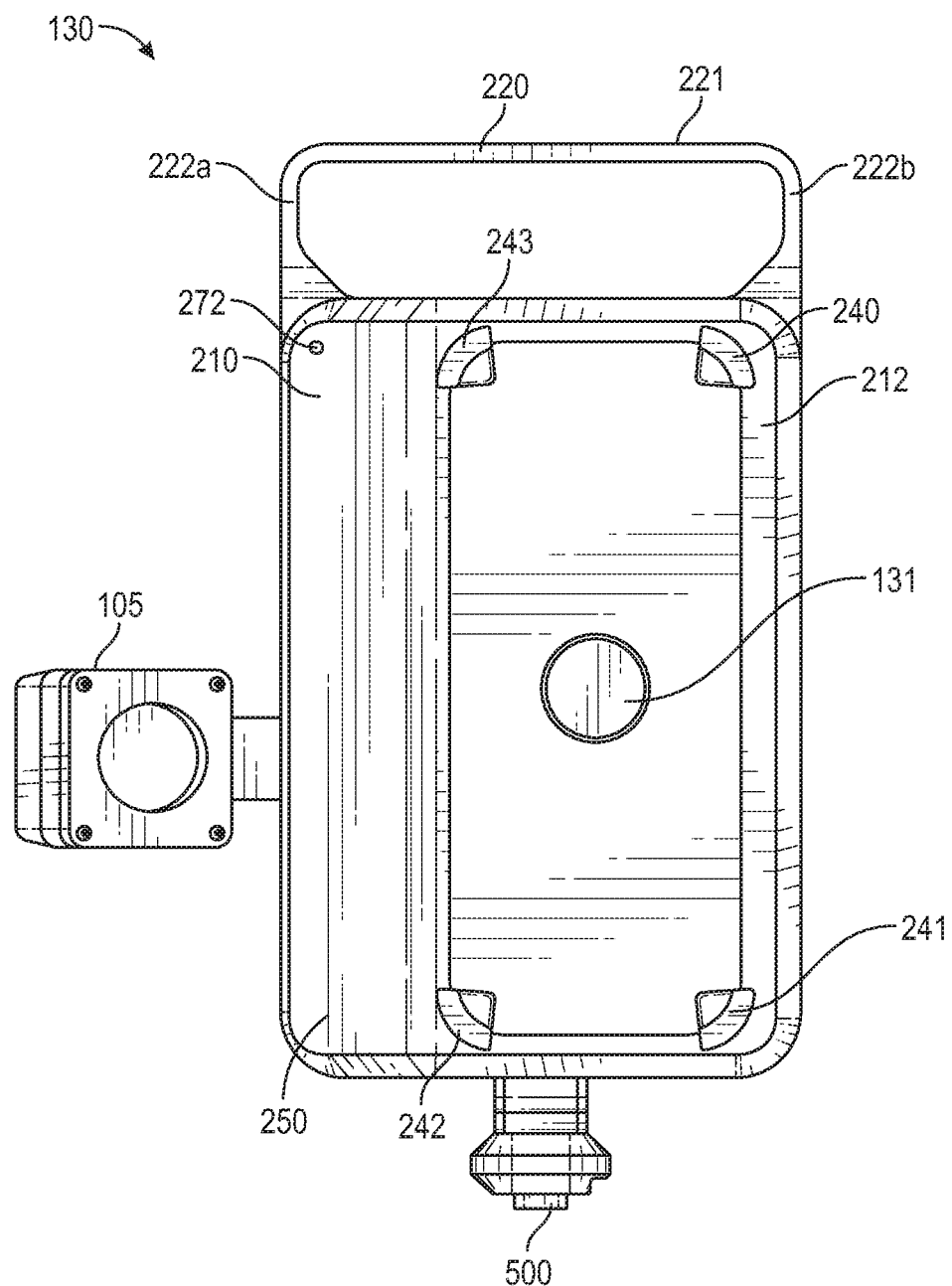
FIG. 2D illustrates a front view of the device of the headset system shown in FIG. 1 according to various arrangements.
Figure 2E:
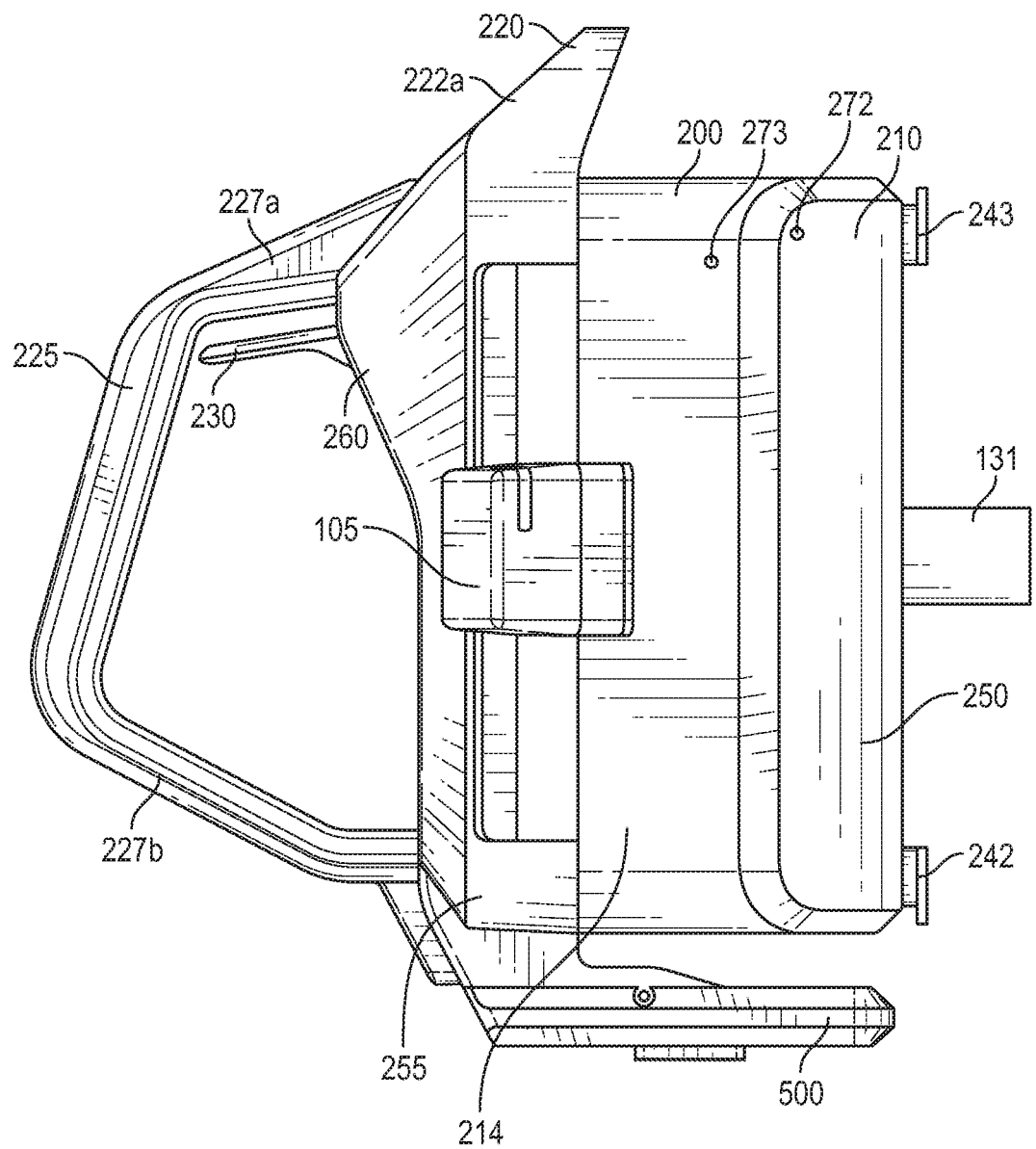
FIGS. 2E and 2F illustrate side views of the device of the headset system shown in FIG. 1 according to various arrangements.
Figure 2F:
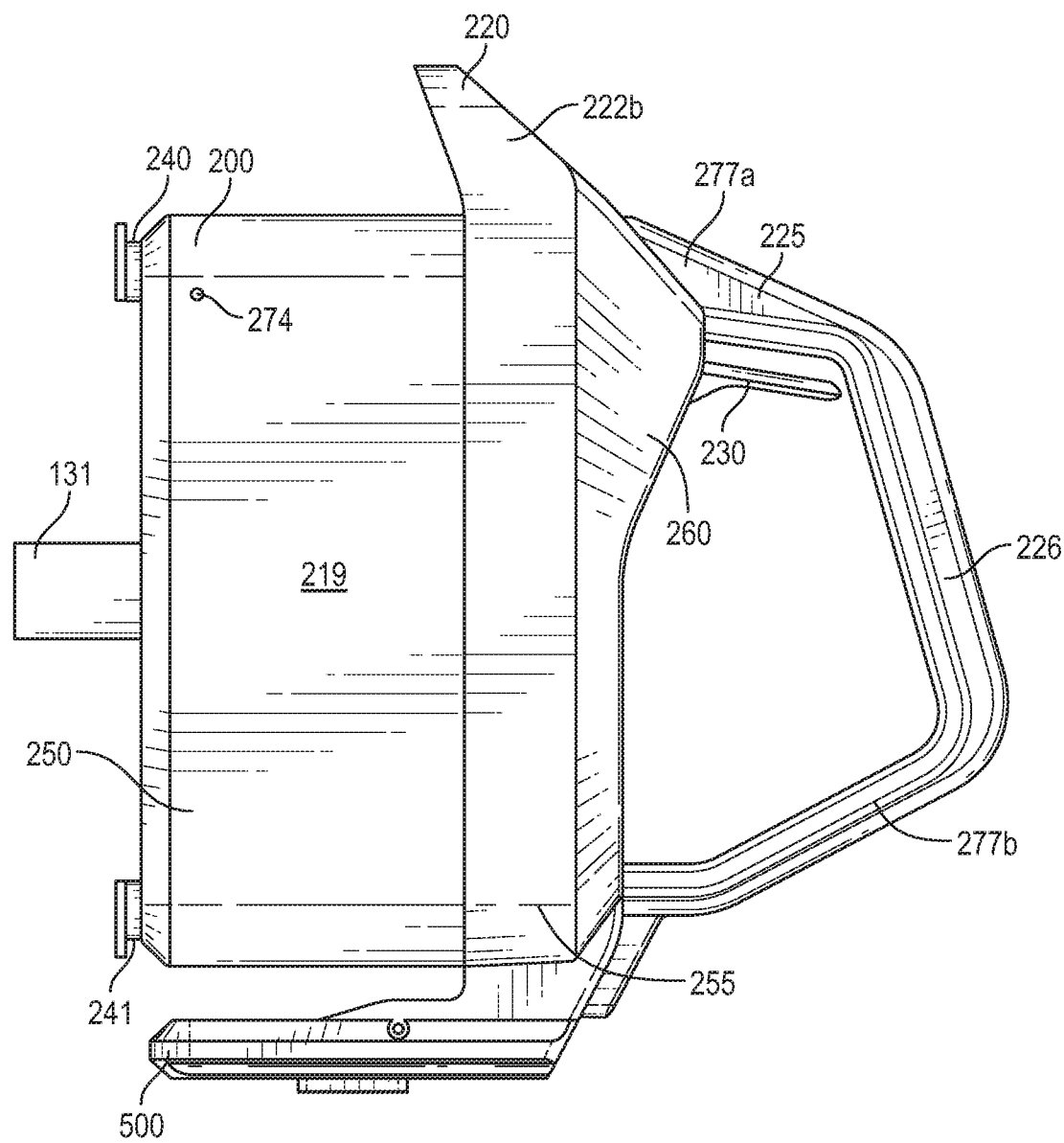
Figure 2G:
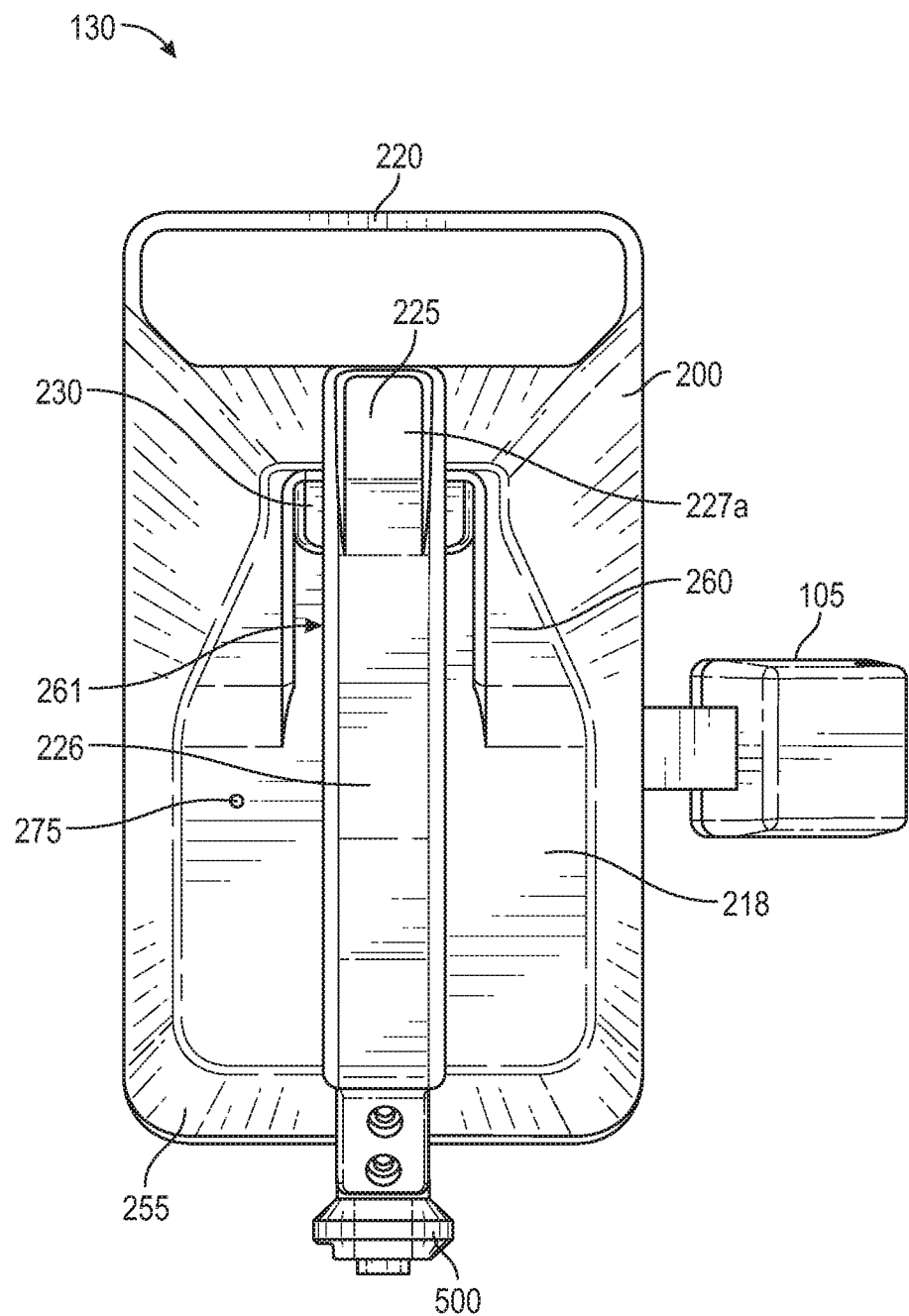
FIG. 2G illustrates a back view of the device of the headset system shown in FIG. 1 according to various arrangements.
Figure 2H:
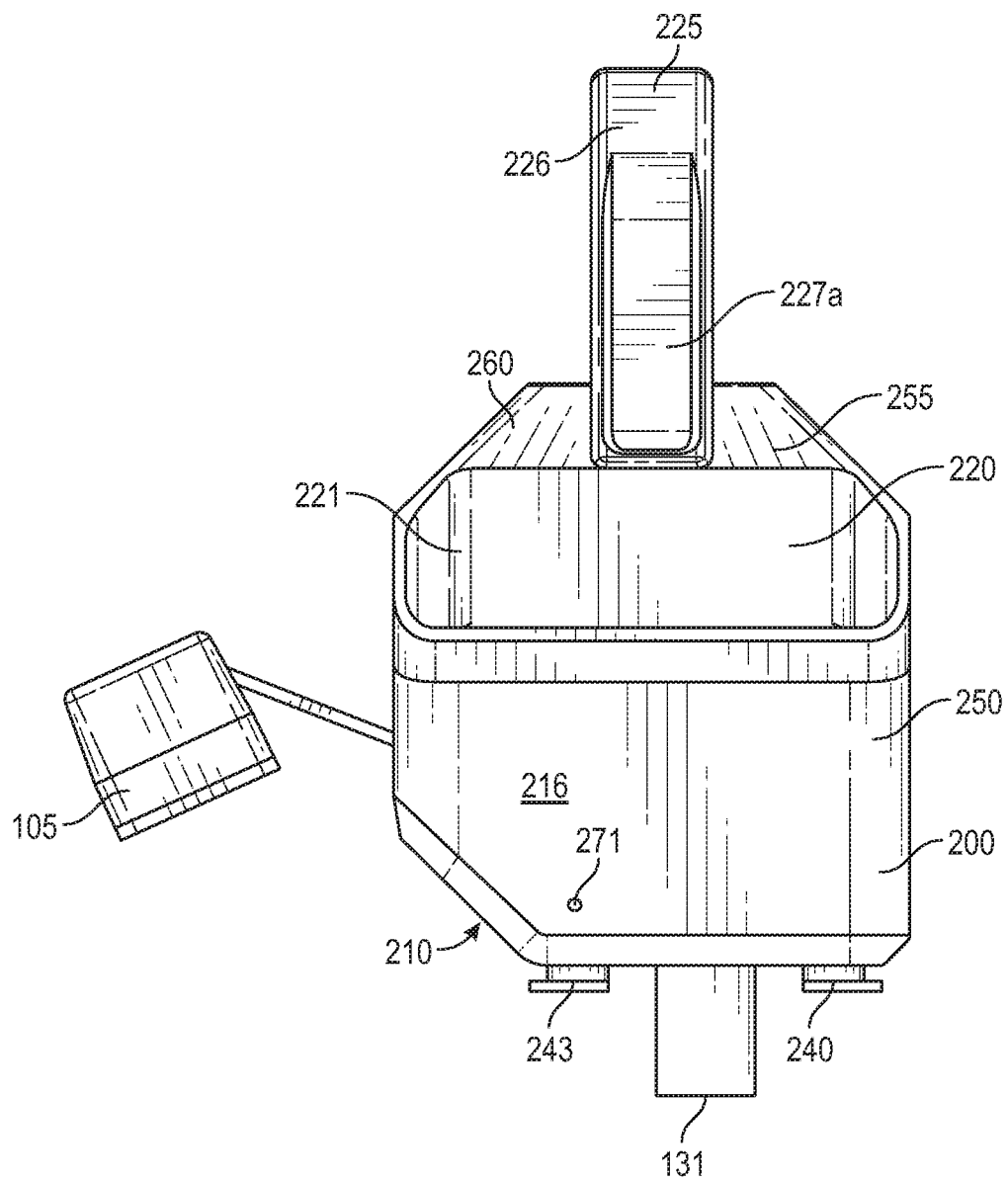
FIG. 2H illustrates a top view of the device of the headset system shown in FIG. 1 according to various arrangements.
Figure 2I:
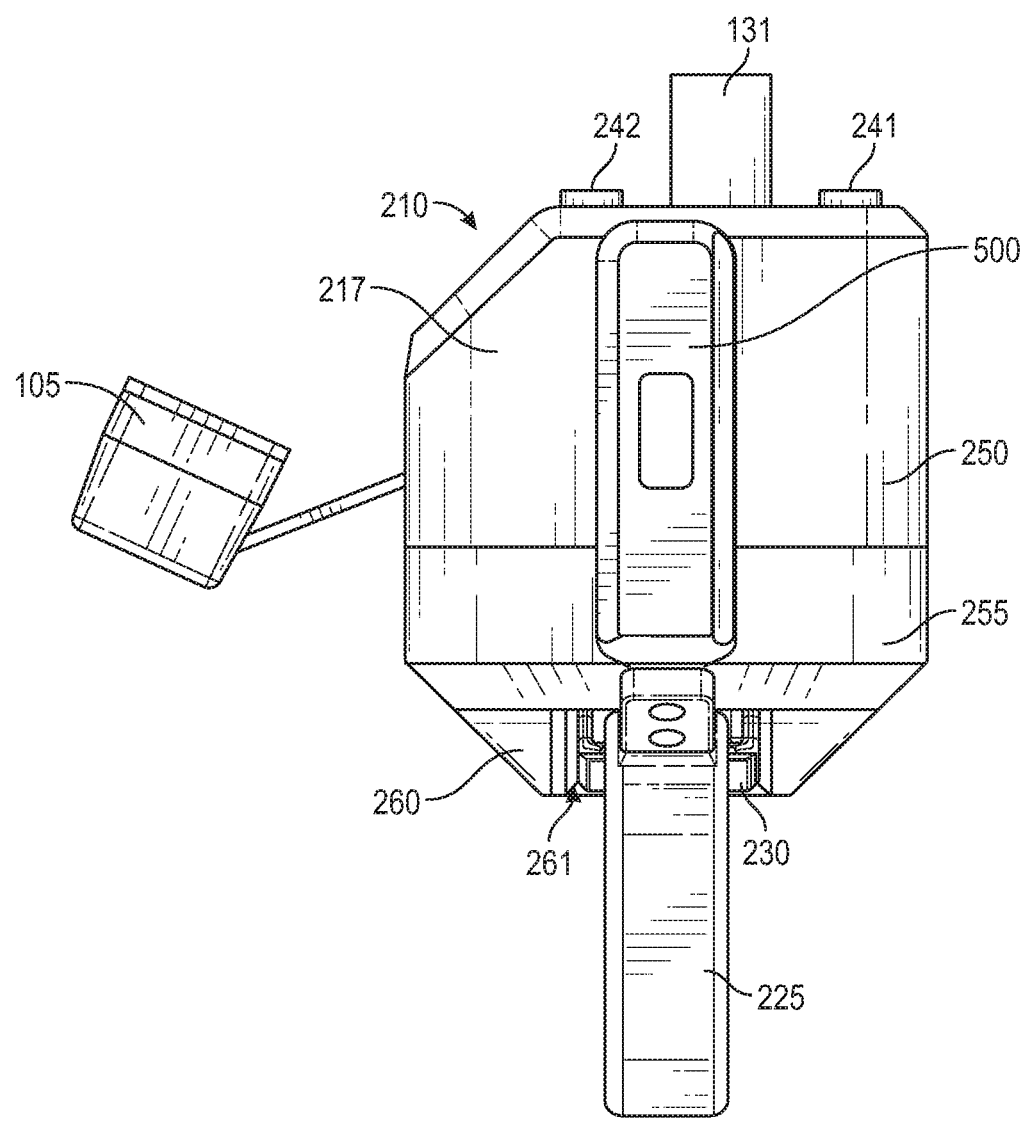
FIG. 2I illustrates a bottom view of the device of the headset system shown in FIG. 1 according to various arrangements.

FIGS. 2A-2C illustrate perspective views of the device 130 shown in FIG. 1 according to various arrangements. FIG. 2D illustrates a front view of the device 130 shown in FIG. 1 according to various arrangements. FIGS. 2E and 2F illustrate side views of the device 130 shown in FIG. 1 according to various arrangements. FIG. 2G illustrates a back view of the device 130 shown in FIG. 1 according to various arrangements. FIG. 2H illustrates a top view of the device 130 shown in FIG. 1 according to various arrangements. FIG. 2I illustrates a bottom view of the device 130 shown in FIG. 1 according to various arrangements.

Figure 3A:
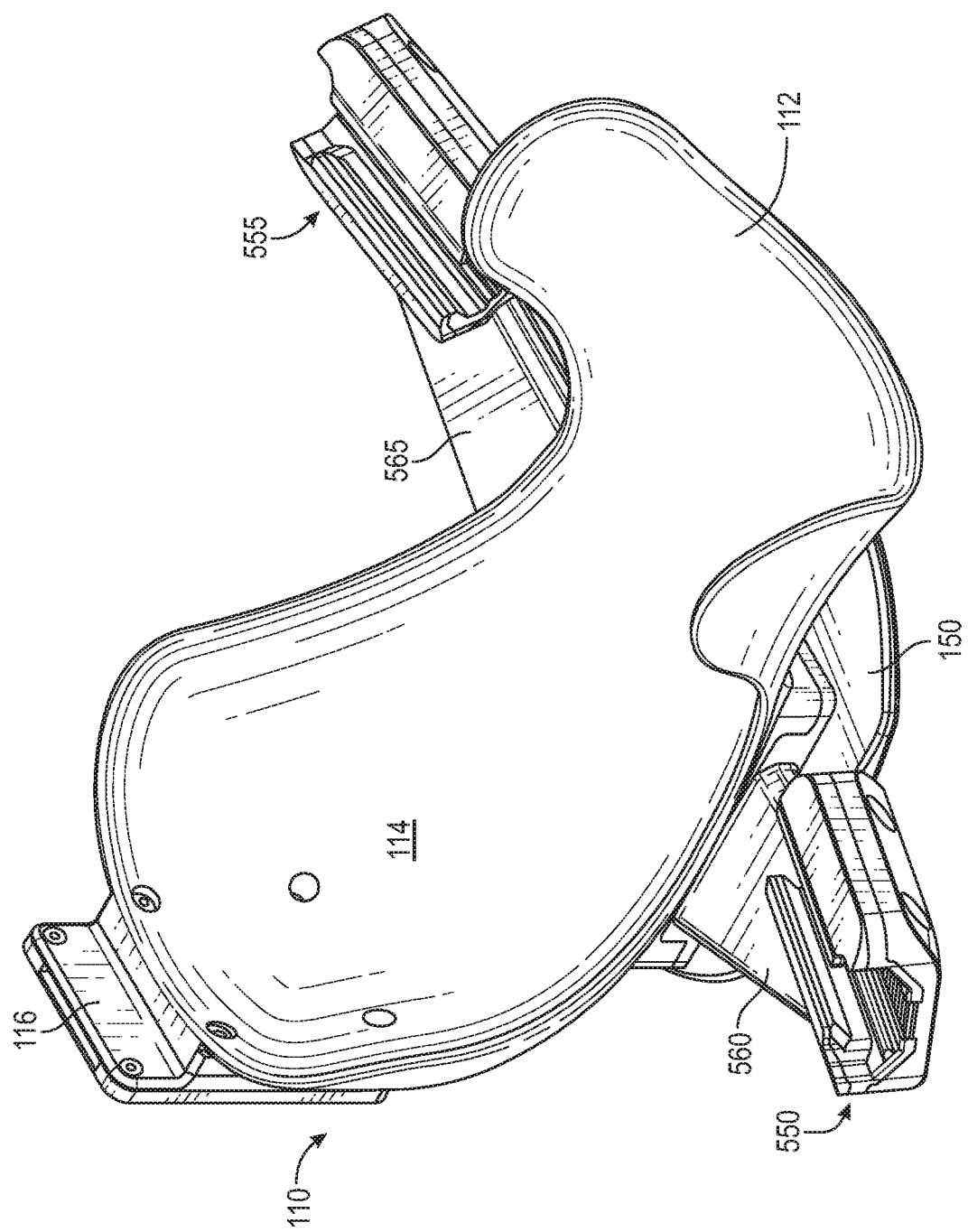
FIG. 3A illustrates a perspective view of the support structure of the headset system shown in FIG. 1 according to various arrangements.
Figure 3B:
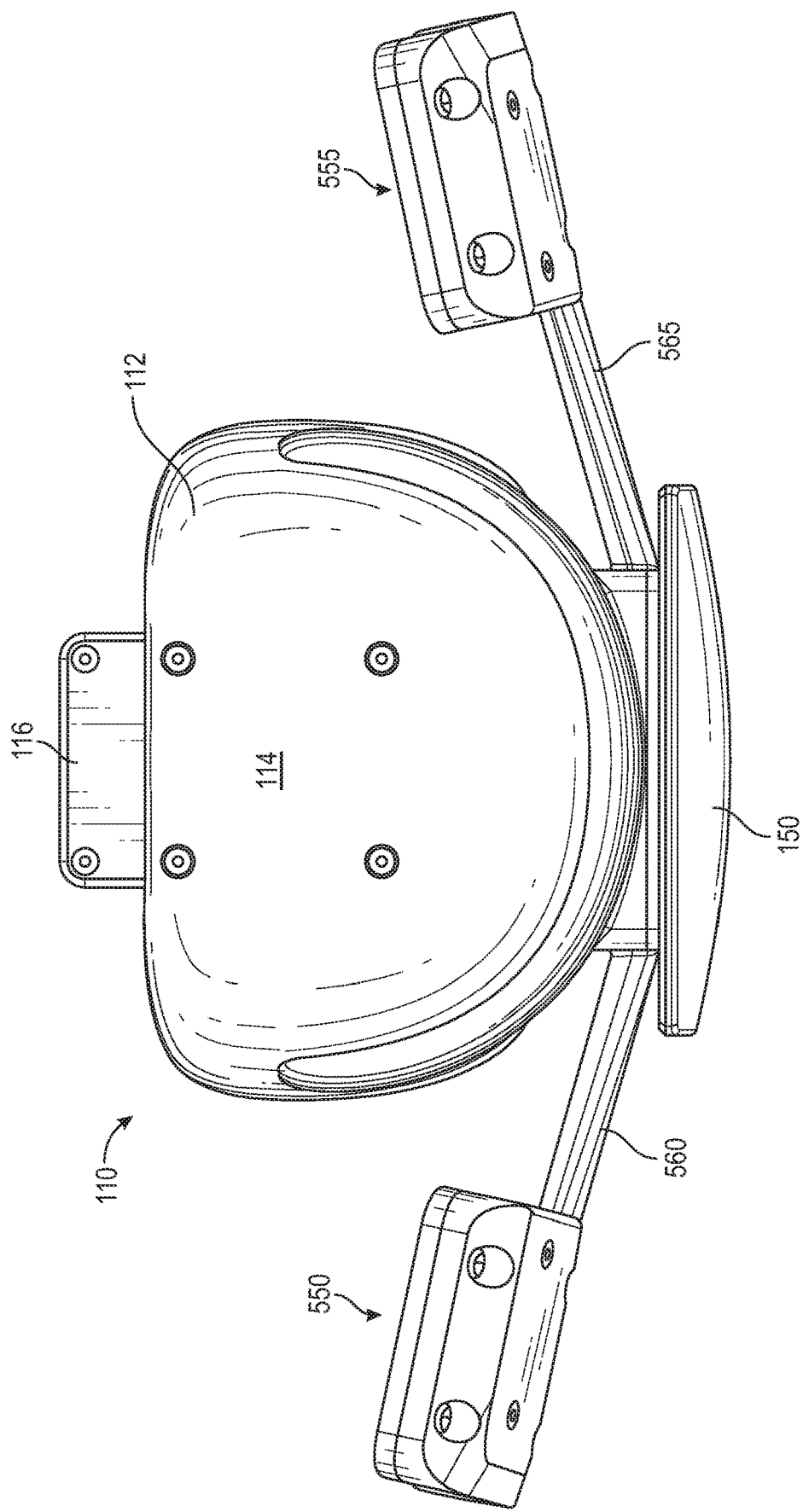
FIG. 3B illustrates a front view of the support structure of the headset system shown in FIG. 1 according to various arrangements.

FIG. 3A illustrates a perspective view of the support structure 110 shown in FIG. 1 according to various arrangements. FIG. 3B illustrates a front view of the support structure 110 shown in FIG. 1 according to various arrangements. FIG. 3C illustrates a side view of the support structure 110 shown in FIG. 1 according to various arrangements.

Referring to FIGS. 1-3C, in some arrangements, the headset system 100 is a modular device such that the devices 130 and 135 can be attached to and detached from the support structure 110 via suitable attachment mechanisms as described herein. In that regard, the headset system 100 can be assembled and dissembled without any tools by an operator, allowing the headset system 100 to collect physiological data on the fly while needing an insignificant amount of time to assemble. The headset system 100 can therefore be deployed in emergency situations in which quick assembly and disassembly are preferred or even required. In some arrangements, the headset system 100 is used in conjunction with a medical device (e.g., the devices 130 and 135) for use with respect to a head of a subject. Examples of such a medical device include but are not limited to an ocular monitoring system, a breathing device, a device for monitoring neurological activity, a surgical device, a device for monitoring radioactive traces, and so on. In other arrangements, the headset system 100 can be used in conjunction with a non-medical device (e.g., a virtual reality eyepiece) for use with respect to a head of the subject.

The device 130 can be positioned to be adjacent to a right lateral side of a head of the subject while the device 135 can be positioned to be adjacent to a left lateral side of the head, when the head is supported by the support structure 110. As such, the devices 130 and 135 may operate simultaneously to collect the physiological data from both sides of the head simultaneously. In that regard, the device 135 may be a mirror-image device of the device 130. As such, while the features of the device 130 are described throughout the application, the features of the device 130 or the mirrored arrangements thereof are likewise features of the device 135. While the two devices 130 and 135 are shown in FIG. 1, the headset system 100 may include one or three or more devices, each of which may be a device such as but not limited to, the device 130 or 135.

In some arrangements, the device 130 includes a probe or transducer 131 and robotics (not shown) for controlling the transducer 131. The transducer 131 and the robotics may be collectively referred to as an "instrument." In that regard, an instrument as used herein refers to at least one data collection device (e.g., a probe such as but not limited to, the transducer 131) and devices (e.g., positioning components such as but not limited to, the robotics and a controller with suitable processing and memory capabilities) configured to control positioning and operations (e.g., data collection) of the device 130. The robotics are configured to translate the transducer 131 along a surface of the head and to move the transducer 131 with respect to (e.g., toward and away from) the head along various axes in the Cartesian, spherical, and rotational coordinate systems. For example, the robotics can include a multiple degree-of-freedom (DOF) positioning system with motion planning. In some arrangements, the robotics are capable of supporting two, three, four, five, or six DOF movements of the transducer 131 with respect to the head. For example, the robotics are configured to translate the transducer 131 along a surface (defined by an XY-plane as further discussed herein) of a head and to move the transducer 131 toward and away (defined by a Z-axis as further discussed herein) from the head. As such, the robotics are configured to move the transducer 131 along multiple axes (e.g., an X-axis, a Y-axis, and a Z-axis), as described herein. The X-axis is perpendicular to or at least transverse to the XY-plane. In some instances, the robotics can translate in X and Y axes (e.g., along a surface of the head) to locate a temporal window region, and in Z-axis with both force and position feedback control to both position and maintain an appropriate force against the head (e.g., a skull/skin of the head) to maximize signal quality by maintaining appropriate contact force. Two angular DOF (e.g., pan and tilt) may be used to maximize normal insonation of blood vessels to maximize velocity signals.

In some arrangements, the transducer 131 includes a first end and a second end that is opposite to the first end. In some arrangements, the first end includes a concave surface that is configured to be adjacent to or contact a scanning surface (e.g., a head of a subject). The concave surface is configured with a particular pitch to focus generated energy toward the scanning surface. In some arrangements, the device 130 is a Transcranial Doppler (TCD) apparatus such that the first end of the transducer 131 is configured to be adjacent to or contact a human head (e.g., a side of the human head), where the transducer 131 is aligned along the head. The first end of the transducer 131 is configured to provide ultrasound wave emissions from the first end and directed into the human head (e.g., toward the brain). In that regard, the transducer 131 is an ultrasound probe (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck. In other arrangements, the transducer 131 is configured to emit other types of waves during operation, such as, but not limited to, infrared (IR), x-ray, electromagnetic, thermal, near-infrared spectroscopy (NIRS), optical, lighting, audio, electroencephalography, or the like.

In some arrangements, a second end of the transducer 131 interfaces with the robotics. The robotics include components, such as, but not limited to, a motor assembly and so on for controlling the transducer 131 (e.g., control Z-axis pressure, normal alignment, and so on). In some arrangements, the registration of the transducer 131 against a subject's head is accomplished using the robotics to properly position and align the transducer 131 with the subject's head or anatomical features thereof. In some arrangements, the second end of the transducer 131 includes a threaded section along a portion of the body of the transducer 131, and the second end is configured to be secured or otherwise operatively coupled to the robotics via the threads (e.g., by being screwed into the robotics). In other arrangements, the transducer 131 is secured or otherwise operatively coupled to the robotics by any other suitable connecting elements such as but not limited to, welding, adhesive, one or more hooks and latches, one or more separate screws, press fittings, or the like.

Further disclosure regarding the device 130 that can be used in conjunction with the headset system 100 described herein can be found in non-provisional patent application Ser. No. 15/399,648, titled ROBOTIC SYSTEMS FOR CONTROL OF AN ULTRASONIC PROBE, and filed on Jan. 5, 2017, which is incorporated herein by reference in its entirety.

In some arrangements, the headset system 100 (e.g., the device 130) supports other medical and non-medical devices that can be used and registered (e.g., positioned or aligned) with respect to a subject's head. For example, in some arrangements, an ocular device is a device that can be optimized by being properly positioned and aligned with a subject's eyes (e.g., if the ocular device is shifted with respect to a subject's eyes, performance of the ocular device may decline). In some arrangements, the ocular device is attached at the headset system 100 so as to cover the eyes of a subject. As an example of a non-medical device use with respect to the headset system 100, in some arrangements, the headset system 100 (e.g., the device 130) can be used in connection with the ocular device that is a virtual reality device configured to provide a virtual experience to the subject such that any disturbance of the positioning of the ocular device in front of the subject's eyes may cause a degradation in the subject's virtual experience.

In some arrangements, the ocular device is a medical device designed to track ocular behavior of a subject such as but not limited to diagnosing whether the subject has experienced a concussion. In other arrangements, the ocular device is an ocular diagnosis or treatment tool for determining or adjusting vision of the subject. As an example, the ocular device is a device for correcting imperfect vision of a subject (e.g., laser eye surgery). As another example, in some arrangements, the ocular device is an ocular diagnostic tool for determining a vision prescription of a subject, presence of one or more eye conditions (e.g., glaucoma, cataracts, ocular hypertension, uveitis, or the like), and so on. In some arrangements, the ocular device is designed to cover and interact with both eyes simultaneously or in sequence. In other arrangements, the ocular device is designed to cover and interact with a single eye (e.g., while the other eye remains uncovered).

The device 130 includes a device housing 200 that houses and protects various electronic and mechanical components of the device 130, including the robotics, at least a part of the transducer 131, a controller for controlling movements and data collection of the transducer 131, and so on. The device housing 200 can be made from any suitable rigid material, such as, but not limited to, hard/rigid plastic, metal, aluminum, steel, titanium, magnesium, various alloys, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, and so on.

The device housing 200 includes a cavity 202 through which the transducer 131 protrudes. The transducer 131 is configured to be moved by the robotics within a boundary defined by the cavity 202. In some examples, the cavity 202 corresponds to (e.g., is parallel with) the XY-plane defined by the X-axis and the Y-axis. The transducer 131 can extend or retract along the Z-axis. The cavity 202 may expose components (e.g., the robotics and the controller) of the device 130.

In some arrangements, the device housing 200 supports a camera 105 on an exterior surface of the device housing 200. The camera 105 is configured to capture one or more images of a subject's head when the subject's head is placed within the support structure 110 (e.g., within a head cradle 112). From the captured one or more images, the subject's head can be registered with respect to the transducer 131. That is, the device 130 is configured to initially position or align the transducer 131 for subsequent operations of the transducer 131 on the subject's head, restricting or defining the workspace (e.g., an actual workspace) of the transducer 131 to certain boundaries during the operations of the transducer 131, and so on.

In some arrangements, the camera 105 is any suitable image capturing mechanism or device for taking images of one or more body parts of the subject (e.g., a subject's head). Examples of the camera 105 include but are not limited to, a digital camera, a thermal camera, an infrared camera, a night vision camera, and so on. In some examples, the camera 105 can have any suitable resolution and focal length for capturing desired images suitable for registering a subject's head. In one example, the camera 105 has about 5 megapixels and about 4 millimeter (mm) focal length. In some arrangements, the resolution and/or the focal length of the camera 105 is fixed or predetermined. In other arrangements, the resolution and/or the focal length are variable and can be altered by an operator or automatically. In some arrangements, an exposure time of the camera 105 is adjustable (e.g., manually adjustable by an operator).

Further disclosure regarding registration can be found in non-provisional patent application Ser. No. 16/132,068, titled SYSTEMS AND METHODS FOR REGISTERING HEADSET SYSTEM, and filed on Sep. 14, 2018, which is incorporated herein by reference in its entirety.

In some arrangements, the support structure 110 includes the head cradle 112 configured to (sized and shaped to) receive and support a subject's head during operation of the devices 130 and 135. The head cradle 112 is sized and shaped to accommodate and supporting different head sizes for use in conjunction with the device 130. In some arrangements, the head cradle 112 includes a frame 114 and padding (not shown for clarity) attached to or disposed over the frame 114. The frame 114 is configured to support the padding. The padding is configured to contact a human head. In other words, the padding is between the frame 114 and the head when the head is supported by the head cradle 112. In some arrangements, the frame 114 is shaped to suitably contour and support varying head sizes and shapes. The frame 114 can also be shaped to adequately position a subject's head in a workspace of the device 130. In some arrangements, the frame 114 of the head cradle 112 is made from any suitably malleable material that allows for flexing, such as, but not limited to, flexible plastics, polyethylene, urethanes, polypropylene, ABS, nylon, fiber-reinforced silicones, structural foams, or the like.

In some arrangements, the padding of the head cradle 112 is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like. The padding of the head cradle 112 has any suitable firmness for supporting a head, such as, but not limited to, in a range of about 0.1 pound per square inch (psi) to about 60 psi, in a range of about 0.1 psi to about 10 psi, or within other suitable ranges of firmness. The padding of the head cradle 112 has memory for expanding to fit contours of a head. In some arrangements, the padding is configured to be compressed and then to expand after the subject's head is placed in the headset system 100 so that the padding expands to secure the headset system 100 (e.g., to fill in a gap between the frame 114 and the head). In some arrangements, the padding is manufactured by any suitable process for affixing the padding to the frame 114 such as but not limited to, injection molding, laminating, adhesive mounting (e.g., gluing or bonding), co-molding, co-casting, injection, snapping, hook-and-loop fastening, friction fitting, attaching with barbs, using screw bosses, and so on. In other arrangements, the padding of the head cradle 112 includes an inflatable bladder.

In some arrangements, the restraint system 120 is configured to restrain a subject's head when the head is in the head cradle 112. In some arrangements, the restraint system 120 includes a body 121 and a contact 122. The body 121 is attached to the support structure 110 (e.g., to one or both of the head cradle 112 and a baseplate 150) via a base 116. As shown, the base 116 includes a cavity configured to receive the body 121 of the restraint system 120. The body 121 of the restraint system 120 includes an elongated section that is configured to slide into the cavity of the base 116 and lock while in the base 116. The body 121 of the restraint system 120 may include a rail of a slide-and-lock mechanism. The body 121 of the restraint system 120 is configured to be locked by the base 116 at different positions along the rail so as to provide adjustability of the restraint system 120 (to adjust a length of the body 121 of the restraint system 120) to accommodate different heads of subjects (e.g., different sizes and shapes). In other examples, the base 116 may include other suitable attachment mechanisms (e.g., snapping, hook-and-loop fastening, friction fitting, latch, and so on) configured to removably connect to the body 121 of the restraint system 120 without tools and to provide adjustability to accommodate different heads of subjects.

In some arrangements, the contact 122 of the restraint system 120 is attached to the body 121 the restraint system 120, and the contact 122 is configured to contact 122 and apply pressure against a subject's head (e.g., forehead) for securing the subject to the head cradle 112. In some arrangements, the contact 122 is configured to pivot at a location where the contact 122 is attached to the body 121 to provide further adjustability for different sized and shaped heads of subjects. In some examples, the contact 122 includes a padding for contacting a subject's head. The padding is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like.

In some arrangements, the baseplate 150 includes the base 116, receiving portions 550 and 555, and the head cradle 112. In some arrangements, one or more of the restraint system 120, the receiving portions 550 and 555, and the head cradle 112 are attached to the baseplate 150 via a plurality of screws and/or bolts. In other arrangements, one or more of the restraint system 120, the receiving portions 550 and 555, and the head cradle 112 are attached to the baseplate 150 by any other suitable connecting elements such as but not limited to, welding, adhesive, one or more hooks and latches, press fittings, or the like. In some arrangements, one or more of the restraint system 120, the receiving portions 550 and 555, and the head cradle 112 are permanently affixed to the baseplate 150. In other arrangements, one or more of the restraint system 120, the receiving portions 550 and 555, and the head cradle 112 are releasably or removably attached to the baseplate 150 without tools.

In some arrangements, the baseplate 150 is made from any suitable rigid material, such as, but not limited to, hard plastic, metals, aluminum, steel, titanium, magnesium, various alloys, rigid plastics, composites, carbon fiber, fiber glass, expanded foam, compression molded foam, SLA or FDM-made materials, RIM molding, ABS, TPO, nylon, PVC, fiber reinforced resins, or the like. The baseplate 150 has a top surface facing and connecting to the head cradle 112. The baseplate 150 has a bottom flat or substantially flat surface opposite to the top surface, the bottom surface facing away from the head cradle 112. The bottom surface is configured to contact a flat work surface (e.g., a bed, a table, the ground, a gurney, and so on) and to stabilize the support structure 110 on the flat surface when the head of the subject is received in the head cradle 112.

Further disclosure regarding the head cradle 112, the base plate 150, and other structural components of the support structure 110 can be found in non-provisional patent application Ser. No. 15/853,433, titled HEADSET SYSTEM, and filed on Dec. 22, 2017, and non-provisional patent application Ser. No. 16/101,352, titled DYNAMIC HEADSET APPARATUS, and filed on Aug. 10, 2018 each of which is incorporated herein by reference in its entirety.

In some arrangements, the device 130 further includes an input device (not shown), an output device (not shown), and a network interface. The input device includes any suitable device configured to allow an operator to input information or commands into the headset system 100. In some arrangements, the input device includes, but is not limited to, a keyboard, a keypad, a mouse, a joystick, a touchscreen display, bottoms, switches, dials, or any other input device performing a similar function. In some arrangements, the output device includes any suitable device configured to display information, results, messages, and so on to an operator concerning the headset system 100. In some arrangements, the output device includes, but is not limited to, a screen, a computer monitor, a printer, a facsimile machine, or any other output device performing a similar function. In some arrangements, the input device and the output device are the same device (e.g., a touchscreen display device). In some arrangements, the network interface 406 is structured for sending and receiving data over a communication network (e.g., results, instructions, requests, software or firmware updates, and so on). Accordingly, the network interface includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like.

In some arrangements, the device 130 further includes the controller/circuits for controlling operations, processing data, executing input commands, providing results, and so on with respect to the device 130. For example, the controller is configured to receive input data or instructions from the input device or the network interface, control the device 130 to execute the commands (e.g., movement and data collection of the transducer 131), receive data from the device 130, provide information to the output device or network interface, and so on. In some arrangements, the controller includes a processor, memory, an image processing circuit, a registration circuit, and a robotics control circuit. The image data captured by the camera 105 is processed by the image processing circuit for registration by the registration circuit. The robotics control circuit controls the robotics to move the transducer 131.

In some arrangements, the processor is implemented as a general-purpose processor and is coupled to at least one memory. The processor includes any suitable data processing device, such as a microprocessor. In the alternative, the processor includes any suitable electronic processor, controller, microcontroller, or state machine. In some arrangements, the processor is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor is implemented as an Application Specific Integrated Circuit (ASIC), one or more Field Programmable Gate Arrays (FPGAs), a DSP, a group of processing components, or other suitable electronic processing components.

In some arrangements, the memory includes a non-transitory processor-readable storage medium that stores processor-executable instructions. In some arrangements, the memory includes any suitable internal or external device for storing software and data. Examples of the memory can include, but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory can store an Operating System (OS), user application software, and/or executable instructions. The memory can also store application data, such as an array data structure. In some arrangements, the memory stores data and/or computer code for facilitating the various processes described herein.

In some arrangements, the device housing 200 is shaped to clear the FOV of the camera 105. For example, the device housing 200 has a chamfered surface 210 having a size and a chamfered angle configured to clear a FOV of the camera 105. The camera 105 is supported on the device housing 200 at a camera position relative to the device housing 200. The camera position corresponds to a lens center of the camera 105. For example, the chamfered surface 210 is formed as a cutout from a vertical edge of the device housing 200, such that the device housing 200 is not in the FOV of the camera 105. In some examples, the device housing 200 has a shape of a rectangular cuboid with surfaces and edges. In some examples, at least a portion of an edge between the camera 105 and the transducer 131 corresponds to the cutout from the device housing 200 to form the chamfered surface 210. In some examples, the cutout edge corresponding to the chamfered surface 210 is between the camera 105 and the support head cradle 112. In some examples, the cutout edge corresponding to the chamfered surface 210 is between the camera 105 and the head of the subject when the head is supported by the support structure 110.

As shown, the chamfered surface 210 has a rectangular shape. In other examples, the chamfered surface 210 may have another suitable shape such as but not limited to, a square, a circle, oval, an irregular shape, and so on. In some examples, the chamfered surface 210 is adjacent to two surfaces of the device housing 200. For example, the chamfered surface 210 is adjacent to a front surface 212 and a back surface 214. The front surface 212 and the back surface 214 are at a 90° angle (or another suitable angle) relative to one another. The cavity 202 is on the front surface 212. As described, the transducer 131 extends from the cavity 202. In one example, the chamfered surface 210 is at a 45° angle relative to the front surface 212 and the back surface 214. In another example, the chamfered surface 210 is at other suitable angles relative to the front surface 212 and the back surface 214. The angle of the chamfered surface 210 can be any suitable angle that allows the device housing 200 to clear the FOV of the camera 105.

The chamfered surface 210 allows the head of the subject to be more visible to the camera 105 when the head is supported by the support structure 110 while keeping the camera 105 as close to the device housing 200 as possible. The camera 105 being as close to the device housing 200 as possible minimizes the risk of the camera 105 being deformed or dislocated due to objects and operators coming into contact with the camera 105 during transportation, storage, or usage, as the camera 105 extends from the device housing 200. Implementing the chamfered surface 210 instead of making the device housing 200 smaller allows the device housing 200 to have as much interior space as possible for structuring supporting the robotics, the transducer 131, the controller, the latch mechanism as described herein, and other components of the device 130 while clearing the FOV of the camera 105.

In some arrangements, the camera position enables the camera 105 to capture image data of at least a portion of the head of the subject. As shown, the camera 105 is configured to capture image data at least a right lateral side of the head. The camera position is optimized relative to the position of the transducer 131 relative to the head or one or more anatomical features thereof.

In some arrangements, the camera position of the camera 105 is adjustable with respect to the device housing 200 to the image data of the subject's head from different positions relative to the device housing 200. That is, the camera 105 can be moved (e.g., pivoted, rotated, shifted, extended, and so on) automatically by the controller or manually by an operator such that locations of particular anatomical features of the subject's head are within the FOV of the camera 105 when the subject's head is supported by the head cradle 112, and such that the device housing 200 or any other portion of the headset system 100 does not obstruct the field of view of the camera 105. The device housing 200 includes suitable movement mechanisms such as but not limited to, motors can move the camera 105 in motions such as pivoting, rotating, shifting, extend, and so on relative to the device housing 200. In the arrangements in which the camera position is adjustable, the camera position as used herein refers to a home position of the camera 105. The home position of the camera 105 is a default position relative to the device housing 200 such that the camera 105 is initially positioned at the home position before the registration process begins with respect to a new subject. That is, every time the device 130 is configured to collect physiological data of a new subject, the camera 105 is initially positioned at the home position before the registration.

In other arrangements, the camera 105 extends from the device housing 200 and is rigidly mounted to or is fixed with respect to the device housing 200, such that the camera 105 is stationary relative to the housing 200. The device housing 200 or any other portion of the headset system 100 does not obstruct the field of view of the camera 105. Movement mechanisms such as motors are not needed to move the camera 105, thus allowing the device 130 to be space-efficient.

In some examples, the camera position (e.g., direction/angle and distance) of the camera 105 relative to the subject's head (e.g., within a predetermined range of sizes/shapes of human heads) is a known parameter. The camera position of the camera 105 relative to the workspace of the transducer 131 is also a known and fixed parameter. Such parameters can be used to register the transducer 131 with respect to the subject's head, as further discussed herein.

To accurately and efficiently register the device 130 for operations, anatomical features of interest such as but not limited to, the subject's temporal regions, tragus, and eye on a lateral side (e.g., the right lateral side) of the subject's head as well as markers indicative of those anatomical features need to be visible to the camera 105 (at the camera position) when the subject's head is supported by the head cradle 112, irrespective of a size or shape of the head of the subject. In some examples, the anatomical features of interest and the markers (fiducials) indicative of those anatomical features are centered in images collected by the camera 105 irrespective of a size or shape of the head of the subject.

Figure 4A:
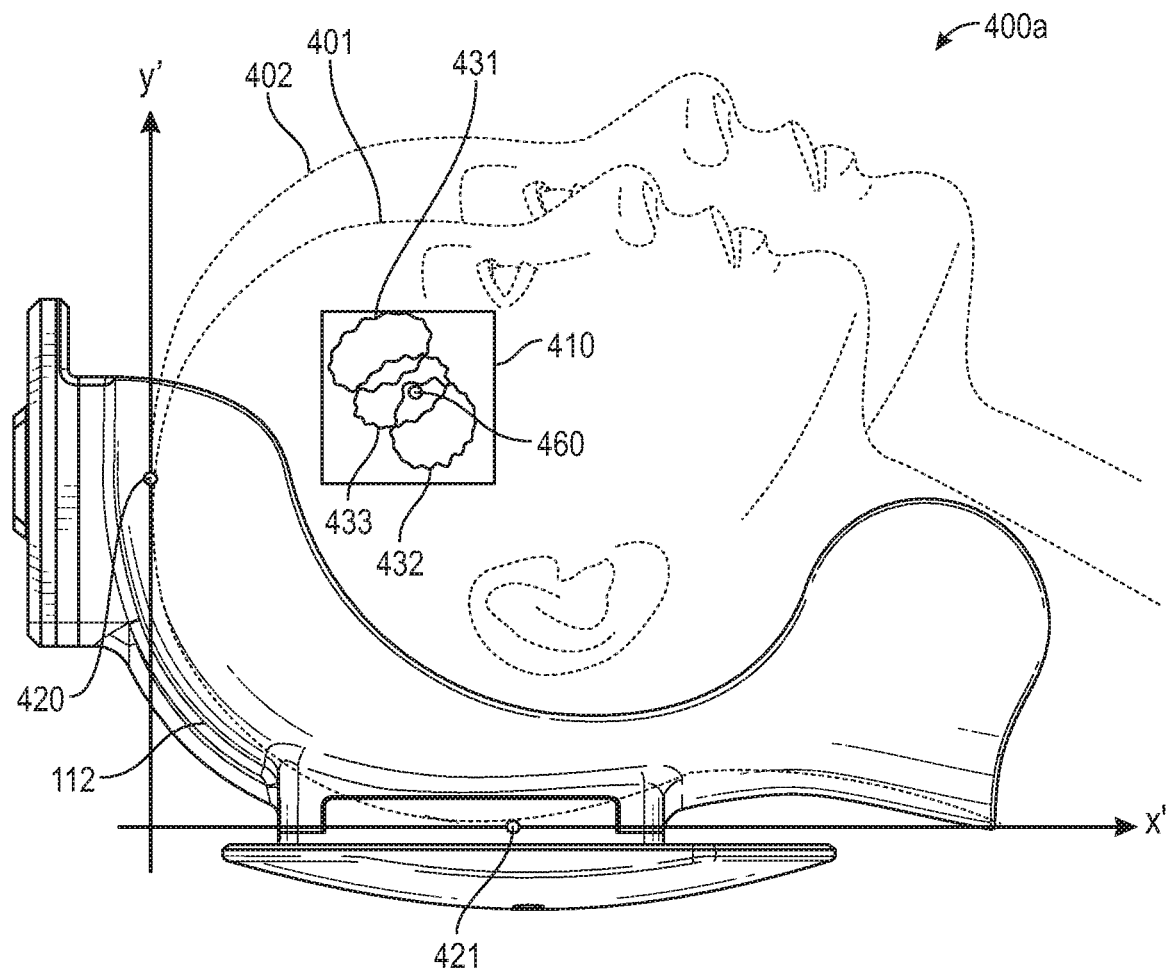
FIG. 4A is a schematic diagram illustrating an objective workspace of a transducer with respect to different sizes and shapes of human heads according to various arrangements.

In that regard, FIG. 4A is a schematic diagram 400a illustrating an objective workspace 410 of the transducer 131 with respect to different sizes and shapes of human heads 401 and 402 according to various arrangements. Referring to FIGS. 1-4A, human heads may have different shapes and sizes. The head cradle 112 is configured (shaped and sized) to support a human head having a size/shape within a range of sizes and shapes of normal human heads. In some examples, all normal human heads have sizes and shapes within the range. In other examples, a predetermined percentage (e.g., 99.9%, 99.5%, 99%, 98%, 95%, and so on) of all normal human heads have sizes and shapes within the range. To illustrate this point, the human head 401 represents one end of the range of sizes and shapes of normal human heads (e.g., the human head 401 is the smallest normal human head in the range) while the human head 402 represents the other end of the range (e.g., the human head 402 is the biggest normal human head in the range). The heads 401 and 402 being supported by the head cradle 112 demonstrates that the head cradle 112 is capable of supporting human heads of any shape/size within the range of normal human heads.

As shown, given the geometry of the head cradle 112, the heads 401, 402 and heads of any sizes/shapes in the range can contact known geometric features (e.g., point(s), surface(s), edge(s), and so on) of the head cradle 112, such that the known geometric features can serve as fixed parameters used in empirical studies seeking to define the objective workspace 410 for the range of normal human heads. The geometric features take into account the thickness and the expanding/contracting nature of the padding of the head cradle 112. For sake of clarity, the padding is not shown. In one example, the known geometric features include a first point 420 and a second point 421 on the head cradle 112. The first point 420 is configured to be adjacent to a crown and/or a mid-scalp region of a head when the head is placed in the head cradle 112. The first point 420 is on the Y'-axis as shown. The second point 421 is configured to be adjacent to a back of the head when the head is placed in the head cradle 112. The second point 421 is on the X'-axis as shown.

Sizes and shapes of normal human heads of test subjects that are within the range are sampled in the empirical studies to define the objective workspace 410. In one example, heads of sample subjects having sizes/shapes within the range were placed in the head cradle 112, and boundaries of anatomical features of interest are determined and recorded. That is, feature boundaries corresponding to at least one anatomical feature of interest (e.g., the temporal regions) are determined for test subjects in at least one empirical study.

When the head 401 is received in the head cradle 112, and the head 401 contacts the head cradle 112 at the points 420 and 421, the anatomical features of interest of the head 401 are within a feature boundary 431. When the head 402 is received in the head cradle 112, and the head 402 contacts the head cradle 112 at the points 420 and 421, the anatomical features of interest of the head 402 are within a feature boundary 432. When another head having a size/shape between the sizes/shapes of the heads 401 and 402 in the range is received in the head cradle 112, and that head contacts the head cradle 112 at the points 420 and 421, the anatomical features of interest are within a feature boundary 433. As shown, the feature boundaries 431-433 correspond to temporal regions of a respective one of the heads 401, 402, and the head having the size/shape between the sizes/shapes of the heads 401 and 402. In other examples, the feature boundaries described herein can also define anatomical features of interest other than the temporal regions.

The boundaries of the objective workspace 410 includes at least the feature boundaries 431-433 as well as the feature boundaries of other subjects having heads of sizes/shapes within the range. In other words, with respect to the anatomical feature of interest (e.g., the temporal region), the objective workspace 410 includes the feature boundaries for all head within the range of sizes and shapes of normal human heads. As shown, the objective workspace 410 is defined on a X'Y'-plane, which is defined by the X'-axis and the Y'-axis. The X'Y'-plane is parallel to the XY-plane. To define the objective workspace 410, the static first point 420 along the Y'-axis can be used to define the objective workspace 410 (e.g., the sample feature boundaries 431-433) with respect to coordinates on the X'-axis. The static second point 421 along the X'-axis can be used to define the objective workspace 410 (e.g., the sample feature boundaries 431-433) with respect to coordinates on the Y'-axis.

The X'Y'-plane is perpendicular to the Z-axis in which the transducer 131 extends. In other examples, the X'Y'-plane is oblique to the Z-axis. The transducer 131 is configured to be moved by the robotics in the XY-plane, which is parallel to the X'Y'-plane. Thus, the total workspace of the transducer 131 is between the X'Y'-plane and the XY-plane along the Z-axis, where the total workspace includes the objective workspace 410 extending from the X'Y'-plane to the XY-plane through the Z-axis.

The device housing 200 and the robotics are configured to support the transducer 131 at a transducer position. The transducer position refers to possible positions of the transducer 131, including a home position of the transducer 131 and scanning positions of the transducer 131. The home position of the transducer 131 is an initial position of the transducer 131 before the transducer 131 begins to collect the physiological data of a subject's head. The robotics are configured to move the transducer 131 to the scanning positions while the transducer 131 collects the physiological data of the subject. That is, the robotics are configured to move the transducer 131 from the home position to the scanning positions. The robotics are configured to move the transducer 131 from a first scanning position of the scanning positions to a second scanning position of the scanning positions.

In some examples, each time after the transducer 131 completes scanning (e.g., collecting the physiological data) a subject, the robotics moves the transducer 131 back to the home position. Thus, before a next subject is scanned, the transducer 131 remains at the home position. In some examples, the home position of the transducer 131 in the XY-plane aligns with or extends toward a center 460 of the objective workspace 410. Both the home position of the transducer 131 and the center 460 of the objective workspace 410 are on the Z-axis. This minimizes the distance that the transducer 131 travels to scan heads with different shapes and sizes because the center 460 of the objective workspace 410 is the closest point to all points in the objective workspace 410.

While the objective workspace 410 is shown to be a square, other shapes (e.g., a rectangle, a circle, an oval, an irregular shape, and so on) of the objective workspace 410 can be likewise determined based on empirical data collected in the empirical studies. In some examples, the objective workspace 410 includes at least an aggregate of all outer contours of the feature boundaries determined in the empirical studies. In some examples, the objective workspace 410 corresponds to an aggregate of all outer contours of the feature boundaries determined in the empirical studies plus a margin (e.g., 5%, 10%, and so on of the dimensions of the aggregate of all outer contours of the feature boundaries).

Figure 4B:
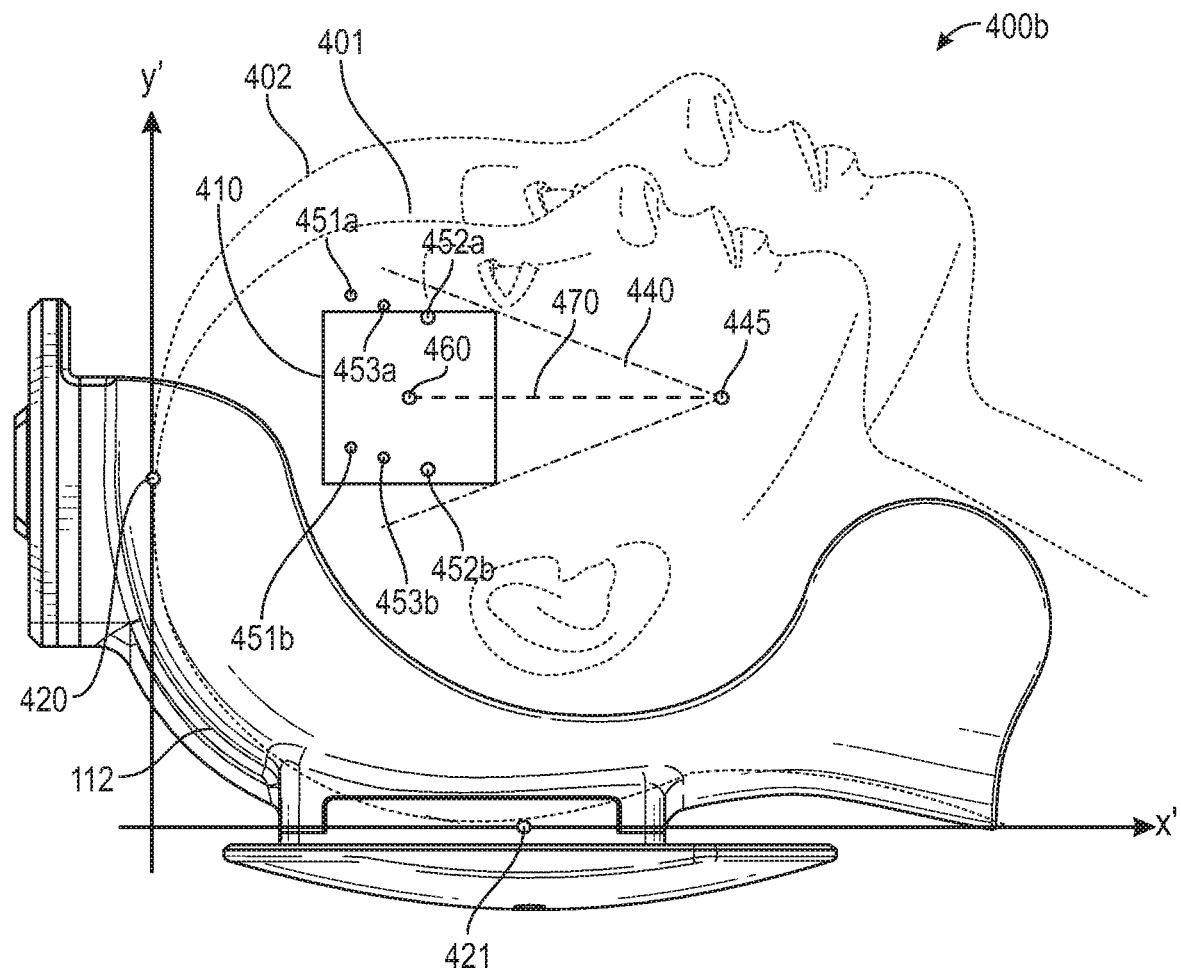
FIG. 4B is a schematic diagram illustrating a FOV of the camera in relation to the objective workspace according to various arrangements.

FIG. 4B is a schematic diagram illustrating a FOV 440 of the camera 105 in relation to the objective workspace 410 shown in FIG. 4A according to various arrangements. Referring to FIGS. 1-4B, the camera 105 is supported at a camera position 445, which corresponds to the lens center of the camera 105. The camera 105 is suitably angled at the camera position 445 to have the FOV 440. As shown, the FOV 440 includes the entirety of the objective workspace 410. This ensures that the camera 105 can capture the image data of the anatomical features of interest. The camera 115 has a line-of-sight (LOS) 470 that passes through the center 460 of the objective workspace 410 as shown. In other examples, the LOS 470 does not pass through the center 460.

The subjects' heads may have markers or fiducial (e.g., fiducials 451a, 451b, 452a, 452b, 453a, and 453b) disposed by an operator at anatomically significant locations such that the image data collected by the camera 105 includes the subject's head with the fiducials. In that regard, for example, the FOV 440 includes fiducials 451a, 451b, 452a, 452b, 453a, and 453b. In some arrangements, the fiducials are disposed at anatomically significant locations (indicative of the anatomical features of interest) to facilitate the controller to determine an actual workspace with respect to a given subject, for example, signifying the boundaries of the actual workspace during operations of the transducer 131.

The objective workspace 410 (moving the objective workspace 410 from the X'Y'-plane to the XY-plane through the X-axis to project the objective workspace 410 onto the XY-plane while maintaining the center 460 on the X-axis) corresponds to a range (aggregate or sum) of the scanning positions and the home position to which the transducer 131 is capable moving. That is, the total workspace represents limits that the transducer 131 can be positioned. The total workspace can he optimized to accommodate as many subjects (having heads of different shapes/sizes) as possible without unnecessarily enlarging the total workspace. Therefore, in determining the total workspace, the range of normal human heads is sampled as used as the basis for the empirical studies. The larger the total workspace is, the larger and more complex the robotics need to be in order to move the transducer 131 within the larger total workspace. The implementations described herein leverage empirical studies to appropriate define the total workspace.

The actual workspace of the transducer 131 is determined for a given subject's head using the registration process, based on the image data collected by the camera 105 as described herein. For example, the feature boundary 431 corresponds to the actual workspace for the human head 401, and the feature boundary 432 corresponds to the actual workspace for the human head 402. Given that a head of each subject may have different sizes/shapes, the actual workspace is determined with respect to each subject so that the transducer 131 can be moved to appropriate scanning positions.

The fiducials are configured to be detected by the image processing circuit. In one example, the fiducials are disposed at a corner of a subject's eye and at the tragus of the subject. As such, to estimate image locations of anatomical markers (e.g., ears and eyes) relative to the transducer 131 through detection of fiducials, at least one image per lateral side of the subject's head can be obtained after placement of at least one fiducial on either lateral side of the subject's head. In other arrangements, fiducials can be any nature anatomy landmarks such as but not limited to, the eyes, the nose, the ear, the forehead, the eyebrow, the mouth, the lips, the hairline, the collar bone, the navel, the nipples, any joints, fingernails, and so on.

In some arrangements, any suitable number of fiducials can be disposed on a subject. In some arrangements, the fiducials are adhesive stickers having a fixed, known, or predetermined size, shape, color, and design to allow the controller to identify the fiducials. In some arrangements, all fiducials disposed on the body of the subject have the same size, shape, color, and design. The controller is preprogrammed with the fiducials characteristics such as the size, shape, color, and design can be used to identify the fiducials from the captured images. In some arrangements, the fiducials include a circular retroreflective material and a surrounding black ring. The circular retroreflective material and the surrounding black ring are on a surface opposite of the surface on which adhesive is provided. The circular retroreflective material and the surrounding black ring are configured to the camera 105 when the fiducials are placed on the subject. For example, the retroreflective fiducials are capable of reflecting light back to a source of the light (e.g., an illumination source installed on the camera 105) with minimal scattering. As an example, an electromagnetic wavefront incident on the fiducials is reflected back along a vector that is parallel to but opposite in direction from the wave's source. Other shapes of the fiducials include but are not limited to, a square, a rectangle, a triangle, a cross, a star, or another complex design that can be easily distinguished from other shapes present on the body of the subject by the controller. An example of a complex design is a square within a circle, which is within a triangle.

The size of the fiducials is a known and controlled parameter that is utilized by the controller during image processing and registration. In some arrangements, each fiducial has a distinctive boundary (e.g., a black boundary) that is made from a material that is not heavily reflective or minimally reflective such that there can be a high contrast between the retroreflective material and its minimally-reflective boundary during illumination of the subject's head (e.g., by the illumination source). The boundary is around an outer perimeter of a fiducial. In some arrangements, each fiducial includes an adhesive backing for application to a subject's skin such that the fiducial remains sufficiently in place during operation of the device 130. Similarly, the color, the shape, and design of the fiducials are known and controlled parameters utilized by the controller during image processing and registration.

As described, the image processing circuit of the controller is configured to receive the image data taken by the camera 105 (e.g., an image depicting a right lateral side of a subject's head), where the scene included in the image data corresponds to the FOV 440. The image captured by the camera 105 includes a two-dimensional array of pixel brightness values. In some arrangements, the registration circuit is configured to transform the camera coordinates obtained by the image processing circuit into robot coordinates for use by the robotics control circuit to control the robotics for positioning the transducer 131 during the operation of the device 130 (e.g., during the scanning and the data collection).

As such, the camera position 445 and the LOS 470 are determined such that fiducial locations corresponding to fiducials placed on test subjects (having head sizes/shapes within the range described) are in the FOV 440. As shown in FIG. 4B, the FOV 440 further includes the fiducials 451a, 451b, 452a, 452b, 453a, and 453b. The fiducials 451a, and 451b are placed on the human head 401 to facilitate in defining boundaries (e.g., the feature boundary 431) of the anatomical features of interest of the human head 401 during the registration process. The fiducials 452a, and 452b are placed on the human head 402 to facilitate in defining boundaries (e.g., the feature boundary 432) of the anatomical features of interest of the human head 402. The fiducials 453a, and 453b are placed on the human head (having a size/shape between the sizes/shapes of the heads 401 and 402) to facilitate in defining boundaries (e.g., the feature boundary 432) of the anatomical features of interest of that human head. Therefore, the fiducials 451a, 451b, 452a, 452b, 453a, and 453b represent a range of fiducial locations for the range of sizes and shapes of normal human heads, when the normal human heads are received in the head cradle 112 and contacting the points 420 and 421. The range of locations of the fiducial locations can be determined using empirical data obtained through empirical studies involving a sufficient sample size. As shown, some of the fiducials (e.g., the fiducials 451a, 452a, and 453a) are on or outside of the boundary of the objective workspace 410 while other fiducials (e.g., the fiducials 451b, 452b, and 453b) are inside of the boundary of the objective workspace 410.

Figure 4C:
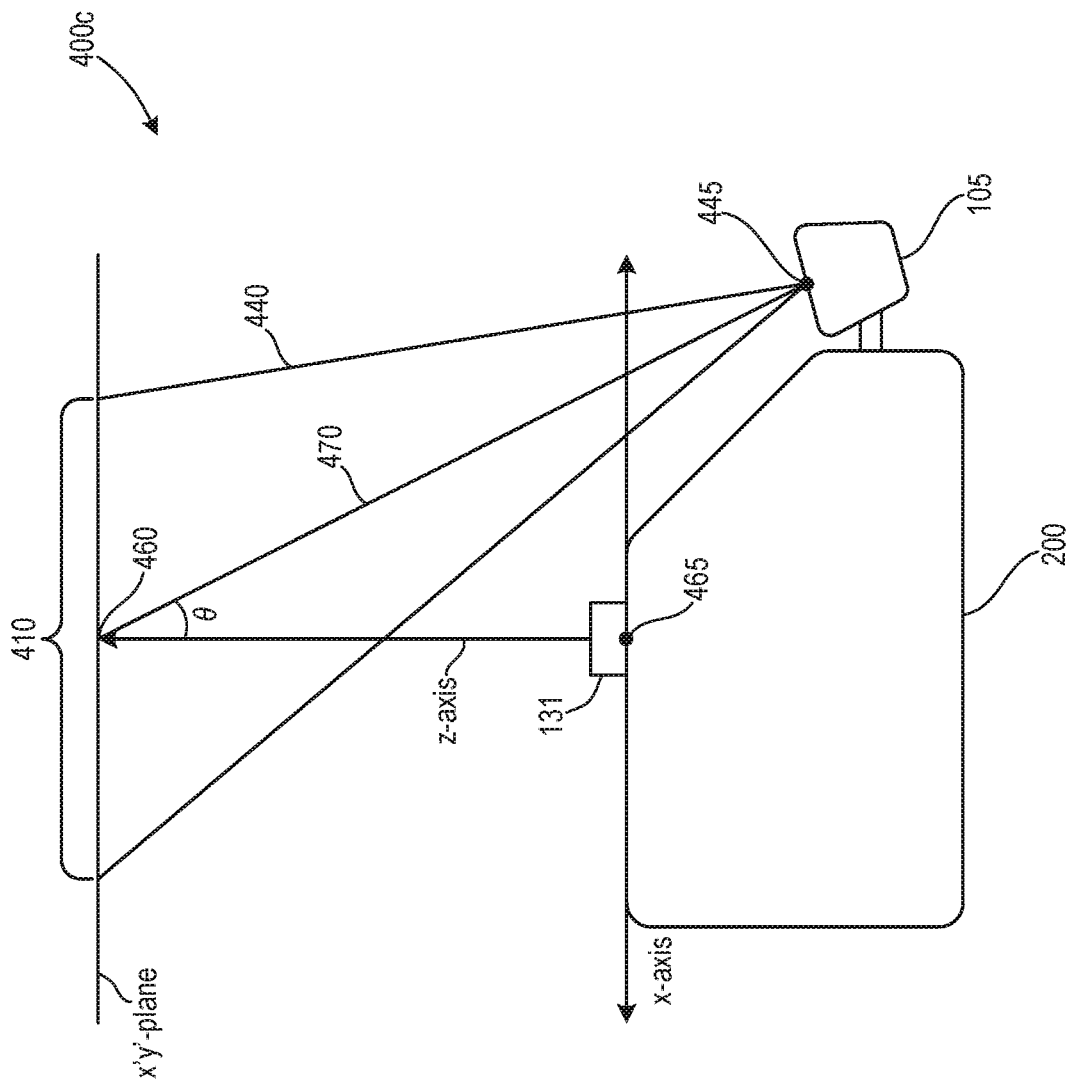
FIG. 4C is a schematic diagram illustrating the FOV of the camera and the home position of the transducer in relation to the objective workspace according to various arrangements.

FIG. 4C is a schematic diagram 400c illustrating the FOV 440 of the camera 105 and a home position 465 of the transducer 131 in relation to the objective workspace 410 according to various arrangements. Referring to FIGS. 1-4C, the schematic diagram 400c shows a top view of the device 130 (e.g., a top surface of the device housing 200 and a top surface of the camera 105). As shown, the transducer 131 is located at the home position 465 and extends in the Z-axis. The Z-axis is perpendicular to the X'Y'-plane and the objective workspace 410. The Z-axis is perpendicular to the XY-plane (including the X-axis as shown), where the XY-plane defines the front surface 212. In some examples, the center 460 of the objective workspace 410 is on the Z-axis. As shown, the center 460 is also on the LOS 470 of the camera 105. The FOV 440 (e.g., the horizontal width of the FOV 440) includes at least the width of the objective workspace 410 as shown. As shown, the LOS 470 extends from the camera position 445 (the lens center) to the center 460 of the objective workspace 410. The LOS 470 is oblique to the objective workspace 410 and the X'Y'-plane. The LOS 470 is at an angle (θ) relative to the Z-axis. The angle θ is implemented so that both the Z-axis and the LOS 470 can pass through the center 460.

Figure 4D:
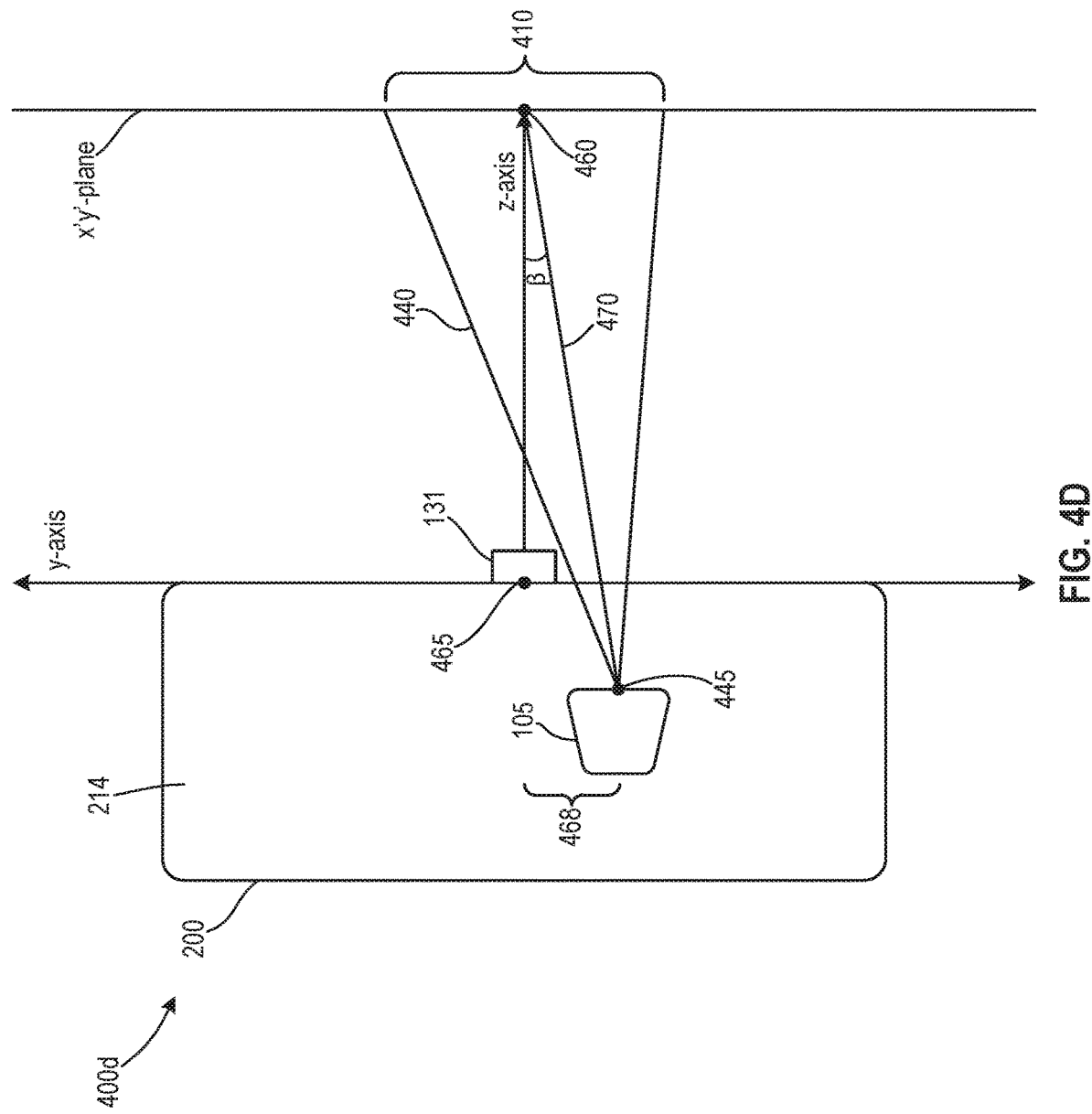
FIG. 4D is a schematic diagram illustrating the FOV of the camera and the home position of the transducer in relation to the objective workspace according to various arrangements.

FIG. 4D is a schematic diagram 400d illustrating the FOV 440 of the camera 105 and the home position 465 of the transducer 131 in relation to the objective workspace 410 according to various arrangements. Referring to FIGS. 1-4D, the schematic diagram 400d shows a side view of the device 130 (e.g., the side surface 214 of the device housing 200 and a side surface of the camera 105). As shown, the transducer 131 is located at the home position 465 and extends in the Z-axis. The Z-axis is perpendicular to the X'Y'-plane, and the objective workspace 410, and the XY-plane (including the Y-axis as shown). In some examples, the center 460 of the objective workspace 410 is on the Z-axis. As shown, the center 460 is also on the LOS 470 of the camera 105. The vertical height of the FOV 440 includes at least the height of the objective workspace 410. As shown, the LOS 470 extends from the camera position 445 (the lens center) to the center 460 of the objective workspace 410. The LOS 470 is at an angle (β) relative to the Z-axis. The angle β is implemented so that both the Z-axis and the LOS 470 can pass through the center 460.

As shown, the home position 465 of the transducer 131 is in a first position (e.g., a first coordinate) on Y-axis, and the camera position 445 is in a second position (e.g., a second coordinate) on Y-axis. Y-axis is a vertical axis extending from a top portion of the device housing 200 to a bottom portion of the device housing 200, where the top portion and the bottom portion are on opposite ends of the device housing 200. The top portion includes a handle 220 and a top surface 216 of the device housing 200. The top surface 216 faces the sky or ceiling when the device 130 is attached to the support structure 110. The bottom portion includes an insert portion 500 and a bottom surface 217 of the device housing 200. The bottom surface 217 faces the insert portion 500 and the flat work surface (e.g., a bed, a table, the ground, a gurney, and the like) when the device 130 is attached to the support structure 110. The distance between the first position and the second position on Y-axis is referred to as an offset distance 468. That is, the camera position 445 is offset from the home position 465 along the vertical axis (Y-axis) by the offset distance 468. Examples of the offset distance 468 include but are not limited to, 5 mm, 10 mm, 15 mm, 20 mm, 1-25 mm, and so on.

Furthermore, as seen in FIGS. 2H, 2I, 4C, and 4D, the camera 105 extends away from the transducer 131 toward a back of the device housing 200 (opposite to where the subject's head may be) such that the FOV 440 of the camera 105 can capture a larger scene (e.g., including at least the objective workspace as described herein) by increasing a length of the LOS 470. As a result, the chamfered surface 210 is implemented to clear the FOV 400 in the manner described.

As shown, the device 130 includes at least a handle (e.g., the handle 220 and a handle 225) disposed on the device housing 200. The handle 220 is rigidly fixed to the device housing 200 and extends from the device housing 200 and forms a grip to allow an operator to grip the handle 220. As such, the device housing 200 (and the device 130) is portable via the handle 220.

As described, the device housing 200 includes the top surface 216 and the bottom surface 217 opposite to the top surface 216. The bottom surface 217 faces in a direction opposite to a direction in which the top surface 216 faces. As described, the bottom surface 217 faces the flat work surface (e.g., a bed, a table, the ground, a gurney, and so on) when the headset system 100 is deployed (e.g., when the device 130 is attached to the support structure 110 and when the baseplate 150 of the support structure 110 is placed on the flat work surface) and collecting the physiological data of the subject. The handle 220 is disposed on the top surface 216.

The device housing 200 may include a front portion 250 and a back portion 255. As shown, the handles 220 and 225 are disposed on the back portion 255. The front portion 250 is configured to structurally support the transducer 131, the robotics, and so on while the back portion 255 is configured to support the camera 105, an actuator 230, the handles 220 and 225, and so on. The front portion 250 and the back portion 255 may be made from different materials. For example, the material of the front portion 250 may be more lightweight than the material of the back portion 255. The material of the back portion 255 may be more heavy-duty given that manual interactive elements such as but not limited to, the handle 220, the handle 225, and the actuator 230 are fixed/coupled to the back portion 255. The material of the back portion 255 being more rigid and durable can reduce wear-and-tear to the manual interactive elements when an operator is carrying the device 130 or actuating the actuator 230 in the manner described. Examples of the material of the back portion 255 include but are not limited to, metal, aluminum, steel, titanium, magnesium, various alloys, and so on. On the other hand, given that the front portion 250 houses at least automated components such as the transducer 131 and the robotics, manual interaction with the front portion 250 is considerably less as compared to that with the back portion 255. Therefore, to reduce overall weight of the device 130, the front portion 250 can be made from a lightweight material such as but not limited to, hard/rigid plastic, carbon fiber, fiber glass, expanded foam, compression molded foam, thermoplastic polymer (e.g., ABS), thermoplastic elastomer (e.g., TPO), nylon, PVC, fiber reinforced resins, and so on. As such, maintenance cost and product lifetime can be improved while the weight of the device 130 is minimized.

In some examples, the front portion 250 and the back portion 255 are configured to move relative to one another. In that regard, the device housing 200 (one or both of the front portion 250 and the back portion 255) may include suitable movement mechanisms such as but not limited to, motors configured to move the front portion 250 and the back portion 255 relative to one another. In some examples, given that the camera 105 is fixed or otherwise coupled to the back portion 255, moving the back portion 255 also moves the camera 105 (e.g., along the X-axis) to change the FOV 440 of the camera 105 (e.g., shifting the FOV 440 along the X-axis).

The handle 220 includes a grip portion 221 and side portions 222a and 222b. The grip portion 221 is configured to be gripped by an operator. The side portions 222a and 222b extend from the device housing 200 (e.g., from the back portion 255) and connect the device housing 200 with the grip portion 221. The grip portion 221 and the side portions 222a and 222b form an arc-like shape and an interior space for a hand of the operator. In the example shown, the grip portion 221 has an elongated shape and extends in a direction that is parallel to the top surface 216, which is the surface of the device housing 200 on which the handle 220 is disposed. In other examples, the grip portion 221 may have another suitable shape and extends in an oblique direction with respect to the top surface 216.

The handle 220 (e.g., at least the side portions 222a and 222b) extends from the device housing 200 in a direction that allows the device housing 200 to be upright (e.g., vertical or substantially vertical to the ground) when the device housing 200 is carried by an operator via the handle 220. In some examples, the handle 220 (e.g., at least the side portions 222a and 222b) extends from the device housing 200 in a direction that maintains a center of mass of the device 130 when the device housing 200 is carried by an operator via the handle 220. In that regard, as shown, the side portions 222a and 222b extends from the back portion 255 in an oblique direction relative to the top surface 216, toward the front surface 212 of the device housing 200 such that when the operator lifts the device housing 200 by the grip portion 221, the center of mass of the device 130 maintains the device 130 housing 200 in an upright position (without tilting to either side). As shown, at least a portion of the grip portion 221 is disposed over the front portion 250. By extending the side portions 222a and 222b in the directions as shown, the weight of the material of the back portion 255 is minimized.

As shown, the device 130 further includes the handle 225 (e.g., a secondary handle) disposed on the device housing 200. The handle 225 is rigidly fixed to the device housing 200 and extends from the device housing 200 to form a grip to allow an operator to grip the handle 225. As such, the device housing 200 (and the device 130) is portable via the handle 225.

The device housing 200 further includes a back surface 218. The back surface 218 is on the back portion 255. The back surface 218 faces in a direction opposite to the direction in which the front surface 212 faces. The handle 225 is disposed on the back surface 218. As described, the transducer 131 protrudes from the front surface 212 and operates within the cavity 202, which is on the front surface 212. The transducer 131 extends toward the support structure 110 to collect the physiological data of the subject when the head of the subject is in the head cradle 112 and when the device 130 is attached to the support structure 110. Further, the insert portion 500 is also configured to extend toward the support structure 110 to engage a receiving portion 550 as described herein to attach the device 130 to the support structure 110. As such, by providing the handle 225 on a surface facing in a direction opposite to the direction in which the transducer 131 and the insert portion 500 extend, the operator has more control when attaching the device 130 (e.g., the insert portion 500) to the support structure 110 (e.g., the receiving portion 550).

The handle 225 includes a grip portion 226 and side portions 227a and 227b. The grip portion 226 is configured to be gripped by an operator. The side portions 227a and 227b extend from the device housing 200 (e.g., from the back portion 255) and connect the device housing 200 with the grip portion 226. The grip portion 226 and the side portions 227a and 227b form an arc-like shape and an interior space for a hand of the operator. In the example shown, the grip portion 226 has an elongated shape and extends in a direction that is oblique to the back surface 218, which is the surface of the device housing 200 on which the handle 225 is disposed. In other examples, the grip portion 226 may have another suitable shape and extends in a parallel direction with respect to the back surface 218. As shown, the direction in which the grip portion 221 extends and the direction in which the grip portion 226 extends are transverse to one another.

As described, the grip portion 226 has a straight and elongated shape and extends in a direction oblique to the back surface 218. The side portion 277a extends from the top portion of the device housing 200 and is proximal to the handle 220. The side portion 277b extends from the bottom portion of the device housing 200 and is proximal to the insert portion 500. The side portion 277b is longer than the side portion 277a. The distance between the grip portion 226 and the back surface 218 is less at locations of the grip portion 226 that are closer to the side portion 277a. The distance between the grip portion 226 and the back surface 218 is greater at locations of the grip portion 226 that are closer to the side portion 277b. This results in the grip portion 226 being oblique with respect to the back surface 218. The shape of the handle 225 allows an operator to manage the position of the device housing 200 in the process of attaching the device 130 to the support structure 110. For example, by gripping the grip portion 226, the operator can easily align the insert portion 500 with the receiving portion 550, improving the assembly time of the headset system 100 and allowing the operator to quickly assemble the headset system 100 in emergency situations.

The back surface 218 and the top surface 216 face different directions and are on different sides of the device housing 200. Therefore, by disposing the handles 220 and 225 on the top surface 216 and the back surface 218, respectively, an operator can carry the device 130 from two different directions.

In some arrangements, the headset system 100 includes an attachment mechanism (connection interfaces) that allows each of the devices 130 and 135 to be releasably and removably attached to the support structure 110 (e.g., the baseplate 150). For example, an insert portion 500 is disposed on the device housing 200 that is configured to be releasably and removably inserted into the receiving portion 550 of the support structure 110. That is, the insert portion 500 is configured (sized and shaped) to engage the receiving portion 550 to removably attach the device housing 200 to the baseplate 150. Likewise, the device 135 (e.g., a device housing such as but not limited to, a mirror image of the device housing 200) includes an insert portion (such as but not limited to, a mirror image of the insert portion 500) configured to be releasably and removably inserted into the receiving portion 555 (such as but not limited to, a mirror image of the receiving portion 550) of the support structure 110. In that regard, the receiving portions 550 and 555 are configured to receive and secure the devices 130 and 135, respectively, using a slide-and-lock mechanism. As shown, the receiving portions 550 and 555 are located on opposite sides of the support structure 110.

In some examples, a body 560 extends in an oblique direction from the baseplate 150. That is, when the bottom surface of the baseplate 150 contacts the flat work surface (e.g., a bed, a table, the ground, a gurney, and so on), the body 560 appears to be raised from the baseplate 150, elevating from the flat work surface farther as the body 560 extends into a receptacle 552. Similarly, a body 565 extends in an oblique direction from the baseplate 150. When the bottom surface of the baseplate 150 contacts the flat work surface, the body 565 appears to be raised from the baseplate 150, elevating from the flat work surface farther as the body 565 extends into a receptacle of the receiving portion 555. The bodies 560 and 565 extend from two opposite sides of the baseplate 150 as mirror images. Directions in which the bodies 560 and 565 extend serve to stabilize the devices 130 and 135 while elevating the receiving portions 550 and 555 to appropriate positions for the operation of the devices 130 and 135 as described.

Furthermore, the receiving portion 550 (e.g., the receptacle 552) extends in a direction that is oblique with respect to and from the baseplate 150. The direction in which the receiving portion 550 (e.g., the receptacle 552) extends is oblique with respect to the flat work surface when the bottom surface of the baseplate 150 contacts the flat work surface. Likewise, the receiving portion 555 (e.g., the receptacle thereof) extends in a direction that is oblique with respect to and from the baseplate 150. The direction in which the receiving portion 555 (e.g., the corresponding receptacle) extends is oblique with respect to the flat work surface when the bottom surface of the baseplate 150 contacts the flat work surface. Directions in which the receiving portions 550 and 555 extend serve to position the devices 130 and 135 to have the appropriate workspaces for the operation of the devices 130 and 135 as described. In some examples, the body 560 extends from the baseplate 150 in a first direction. The receptacle 552 extends in a second direction. The first direction traverses the second direction.

Figure 5A:
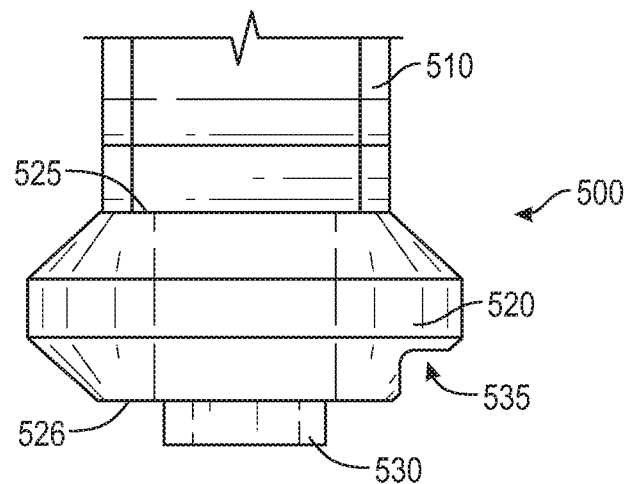
FIG. 5A illustrates a front view of an insert portion of the device shown in FIGS. 1-2I according to various arrangements.
Figure 5B:
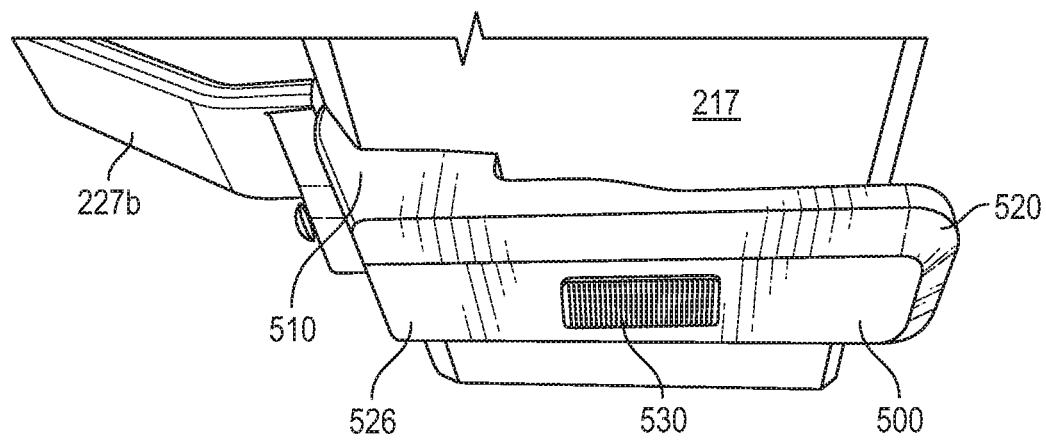
FIG. 5B illustrates a perspective view of the insert portion of the device shown in FIGS. 1 and 1-2I according to various arrangements.
Figure 5C:
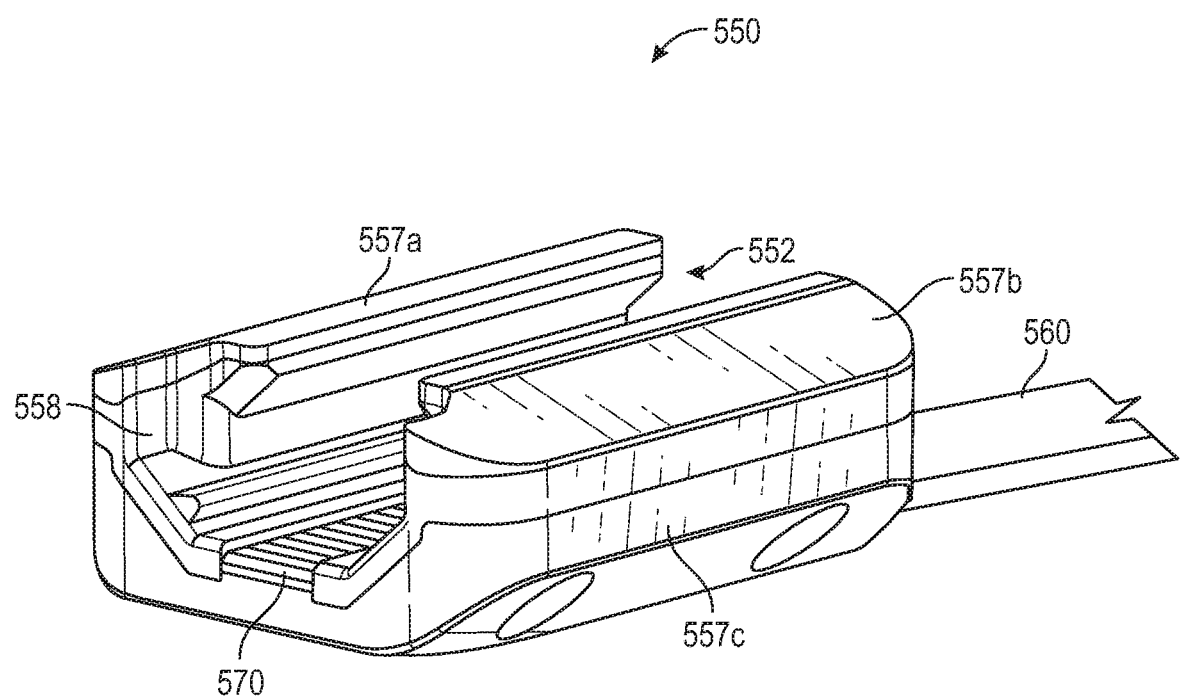
FIG. 5C illustrates a perspective view of the receiving portion of the support structure shown in FIGS. 1 and 3A-3C according to various arrangements.
Figure 5D:
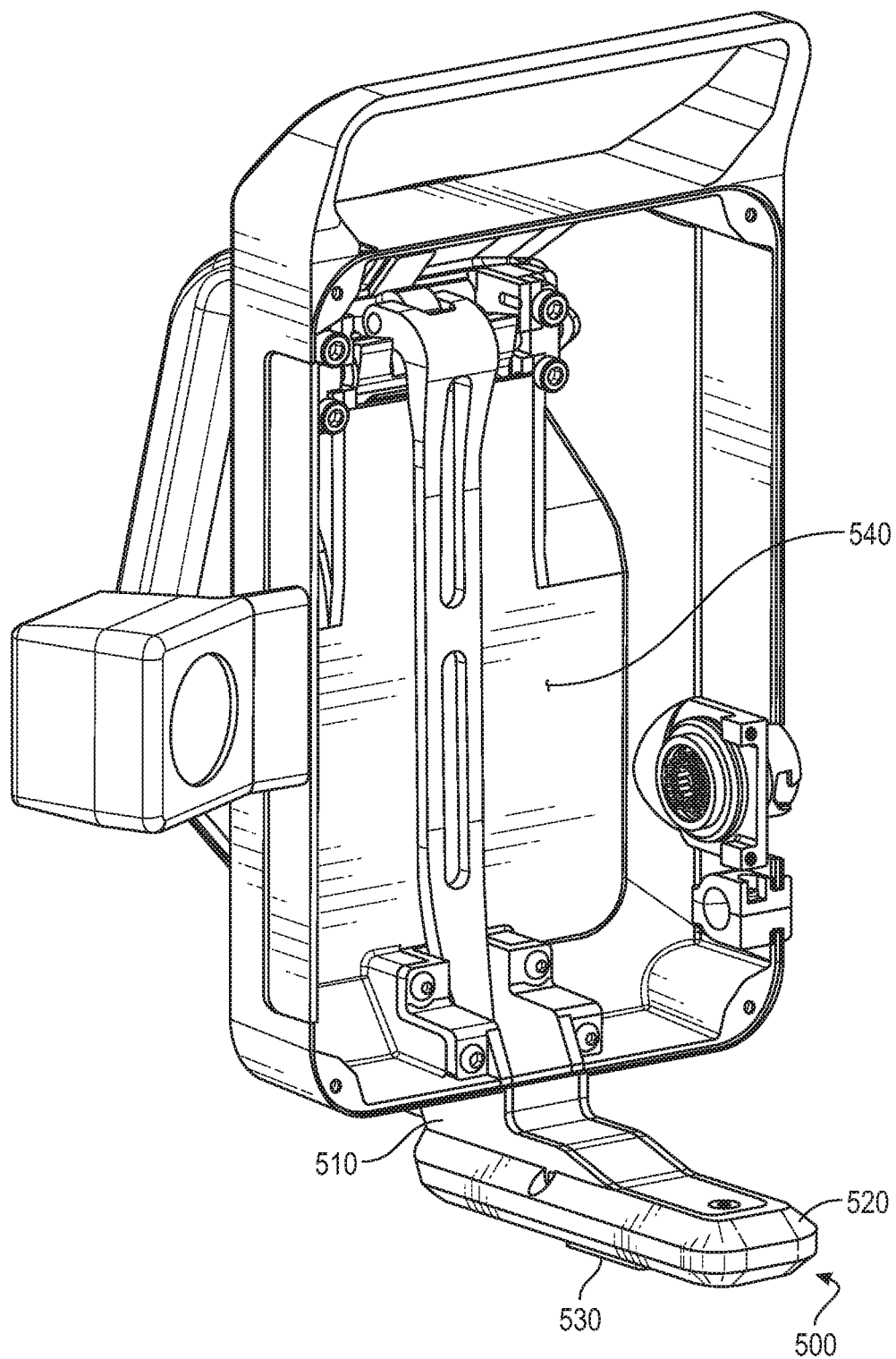
FIG. 5D illustrates a perspective view of a mechanical linkage linking an actuator to a rail according to various arrangements.

FIG. 5A illustrates a front view of the insert portion 500 of the device 130 shown in FIGS. 1-2I according to various arrangements. FIG. 5B illustrates a perspective view of the insert portion 500 of the device 130 shown in FIGS. 1 and 1-2I according to various arrangements. FIG. 5C illustrates a perspective view of the receiving portion 550 of the support structure shown in FIGS. 1 and 3A-3C according to various arrangements. FIG. 5D illustrates a perspective view of a mechanical linkage 540 linking the actuator 230 to a rail 530 according to various arrangements.

Referring to FIGS. 1-5D, in some arrangements, the insert portion 500 is configured as a slider that can slide into the receiving portion 555 to engage tracks (e.g., the slots 570) on the receiving portion 555. The insert portion 500 is configured to be adjustable along the slots 570 of the receiving portion 555. The receptacle 552 forms an aperture configured to receive the insert portion 550. For example, the insert portion 500 can slide within the receptacle 552 and can be locked in place at a desired position relative to the receiving portion 555. The aperture has an inner surface that includes the slots 570.

In some arrangements, given that the device housing 200 is fixed relative to the insert portion 500, adjustment of a position of the insert portion 500 (via the rail 530 having teeth) relative to the receiving portion 550 (the slots 555) results in adjustment of the device housing 200 (e.g., the transducer 131) with respect to a subject's head (e.g., in a telescoping adjustment in a direction in which the extension portion 500 extends). The direction in which the insert portion 500 extends is parallel to the Z-direction toward and away from the subject's head. As described, the transducer 131 extends along the Z-axis toward the head of the subject (e.g., toward the support structure 110) when the head is supported by the support structure 110.

The insert portion 500 includes a first end 510 connected to the device housing 200 and a second end (e.g., an extension 520) opposite to the first end 510. The extension 520 extends from the first end 510 (and from the device hosing 200) in a direction parallel to the direction along the Z-axis in which the transducer 131 extends. In some arrangements, a bottom surface 217 of the device housing 200 is connected to the insert portion 500 (e.g., the first end 510 of the insert portion 500). In particular arrangements, the device housing 200 is affixed to the first end 510 of the insert portion 500 by any suitable connection mechanism, such as, but not limited to, welding, adhesive, one or more separate bolts, one or more hooks and latches, one or more separate screws, press fittings, or the like.

In some arrangements, the insert portion 500 is made from any suitable rigid material, such as, but not limited to, hard plastic, metals, aluminum, steel, titanium, magnesium, various alloys, rigid plastics, composites, carbon fiber, fiber glass, expanded foam, compression molded foam, SLA or FDM-made materials, RIM molding, ABS, TPO, nylon, PVC, fiber reinforced resins, or the like. Considering the use of the insert portion 500, the insert portion 500 is made from metals, aluminum, steel, titanium, magnesium, various alloys, and so on.

As described, the teeth of the rail 530 are configured (sized and shaped) to engage the slots 570 when the insertion portion 500 (e.g., the extension 520) is engaged with the receiving portion 550. At least a portion of the extension 520 can be inserted into the receptacle 552. In some examples, the extension 520 has a substantially flat shape. As better seen in FIG. 5A, the extension 520 has a hexagonal shape with a top surface 525 and a bottom surface 526. The bottom surface 526 faces away from the bottom surface 217 of the device housing 200. The rail 530 is disposed on the bottom surface 526. The flat and hexagonal shape serves to stabilize the extension 520 and the device 130 when inserted into the receptible 552, such that the device 130 does not tilt from side to side during operations of the transducer 131. In addition, the device housing 200 is configured to stand upright on a surface (e.g., the flat work surface) due to the flat shape, if the operator needs to temporarily set the device 130 down. This improves user-friendliness. Further, the extension 520 includes a key portion 535 that makes the front face of the extension 520 asymmetric. The receptacle 552 has a corresponding protrusion therein that fits into the key portion 535. The asymmetry allows the extension 520 to fit into the receptacle 552 but not the extension of the device 135, thus minimizing the changes that the operator installs the device 135 to the receiving portion 550.

The receiving portion 550 may have an inner portion 558 having an inner surface configured to allow the extension 520 to fit therein. Thus, the inner portion 558 has a shape that conforms with the shape of the extension 520. The receiving portion 550 includes outer portions 557a, 557b, and 557c that cover the inner portion 558 to provide structure rigidity. In some examples, the inner portion 558 may be made from a material more flexible than that of the outer portions 557a, 557b, and 557c, to allow the extension 520 to be easily inserted. For example, the inner portion 558 may be made from a hard/rigid plastic, composites, carbon fiber, fiber glass, SLA or FDM-made materials, RIM molding, ABS, TPO, nylon, PVC, fiber reinforced resins, or the like. The outer portions 557a, 557b, and 557c are configured to provide structure integrity and prevent the inner portion 558 from expanding due to overuse. In that regard, the outer portions 557a, 557b, and 557c are made from metals, aluminum, steel, titanium, magnesium, various alloys, and so on. The outer portions 557a, 557b, and 577c are separate from one another. The slots 570 are disposed on the outer portion 577c.

The actuator 230 (a latch) is disposed on the back surface 218 of the device housing 200. As described herein, the actuator 230 is configured to lock the insert portion 500 in a position relative to the receiving portion 550 when at least a part of the insert portion 500 is inserted into the receiving portion 550. The actuator 230 is disposed in a space between the handle 225 and the device housing 200 (e.g., the back surface 218), proximal to the side portion 277a. The handle 225 protects the actuator 230 from wear-and-tear, obstructing objects that would otherwise come into contact with the actuator 230 by forming a protective barrier around the actuator 230. The handle 225 also prevents wires from entangling the actuator 230 by forming the protective barrier around the actuator 230. Furthermore, the position of the actuator 230 allows the operator to use a hand to insert the insert portion 500 into the receiving portion 550 and then to lock the insert portion 500 in place using the same hand. This improves user-friendliness and deficiency in assembling the headset system 100.

As shown, the back surface 218 includes a raised portion 260 forming a slot 261. When the actuator 230 is in a first position (e.g., proximal to the side portion 227a), the rail 530 is in the unlock position (retracted into the extension 520). When the actuator 230 is in a second position (e.g., into to the slot 261), the rail 530 is in the lock position (protruding from the extension 520). The raised portion 260 forms a barrier on either side of the actuator 230 when the actuator 230 is in the second position to prevent the operator or another object from coming into contact with the actuator 230. The width of the actuator 230 allows the actuator 230 to be moved from either side of the handle 225.

The actuator 230 is configured to lock the insert portion 500 in the position relative to the receiving portion 550 by controlling a position of the rail 530. The actuator 230 is configured to control the position of the rail 530 via a lever mechanism (the mechanical linkage 540) connecting or linking the actuator 230 with the rail 530. As shown, the mechanical linkage 540 includes suitable joints and arms configured to transfer mechanical energy from the actuator 230 to the rail 530 to actuate the rail 530 in the lock and unlock positions as described. As shown, the rail 530 is configured to face an opening slit of the receptacle 522 of the receiving portion 550.

In some examples, the insert portion 500 is disposed on the second portion 255 as shown. The insert portion 500 may be made from a same heavy-duty material as that of the second portion 255. The insert portion 500 may be fixed to the second portion 255 via screw bosses, and so on. In other examples, the insert portion 500 may be detachably mounted to the second portion via latches, snapping, hook-and-loop, and so on such that the insert portion 500 can be replaced without tools. In other examples, the insert portion 500 is disposed on the first portion 250. In some examples, the entire insertion portion 500 is detachable from the device housing 200. In other examples, the extension 520 can be detachable from the first end 510 to be replaced.

As described, the transducer 131 is configured to move relative to the subject in collecting the physiological data. For example, the robotics can move the transducer 131 in the Z-axis and along the XY-plane/X'Y'-plane. Before registering (pre-registration) or before scanning the subject (post-registration), the operator may need to manually position the transducer 131 at a half-Z position along the Z-axis using suitable interactive elements (not shown) such as but not limited to, a level, a knob, a dial, a button and so on. The interactive elements are operatively coupled to the transducer 131 and/or the robotics. The half-Z position corresponds to a center on the Z-axis that is between the home position 465 and a farthest position to which the robotics can move the transducer 131 along the Z-axis. The distance (a predetermined length) between the home position 465 and the farthest position is referred to as a maximum Z-axis distance. The half-Z position is at half or approximately half of the maximum Z-axis distance. Failing to move the transducer 131 a sufficient length along the Z-axis to the half-Z position from the home position 465 may result in poor signal quality given that the transducer 131 may be too far away from the head of the subject. On the other hand, moving the transducer 131 past the half-Z position from the home position 465 may result in the subject experiencing increased pressure from the transducer 131 during data collection, causing discomfort or even pain. Thus, the operator should be notified whether the transducer 131 has been moved manually to the half-Z position or to within a predetermined range centered at the half-Z position. In one example, the predetermined range is 5%, 10%, 15%, or so on of the maximum Z-axis distance. In another example, the predetermined range is 5 mm, 1 cm, 1.5 cm, 1 mm-2 cm, or so on.

In that regard, the device housing 200 further includes at least one position indicator (e.g., position indicators 270-275) configured to indicate whether the transducer 131 is at the predetermined position along the Z-axis. For example, the controller (e.g., the processing circuit) is operatively coupled to the position indicators 270-275 to control the position indicators 270-275 in the manner described. The transducer 131 is operatively coupled to a linear encoder (not shown), which is configured to send a signal corresponding to a current position of the transducer 131 along the Z-axis to the controller. For example, the linear encoder may include a position sensor coupled to a scale. The scale may be magnetic, optical, inductive, capacitive, and so on. The scale is operatively coupled (e.g., threaded or paired) to the transducer 131 and moves with the transducer 131. The position sensor is configured to read an output (e.g., an encoded position) from the scale and convert the output into an electrical signal. The controller may include motion controller or a digital readout element configured to decode the signal to obtain the position of the transducer 131 along the Z-axis. As such, the controller is configured to determine whether the current position of the transducer 131 is at a predetermined position (the half-Z position or within the predetermined range centered at the half-Z position) along the Z-axis based on the signal.

The controller is further configured to control the position indicators 270-275 to indicate that the transducer 131 is at the predetermined position along the Z-axis in response to determining that the current position of the transducer 131 is at the predetermined position (the half-Z position or within the predetermined range centered at the half-Z position). For instance, the controller can configure the position indicators 270-275 to indicate that the transducer 131 is at the predetermined position along the Z-axis by controlling the position indicators 270-275 to be in a first displayed state.

In addition, the controller is configured to control the position indicators 270-275 to indicate that the transducer 131 is not at the predetermined position along the Z-axis in response to determining that the current position of the transducer 131 is not at the predetermined position (the half-Z position or within the predetermined range centered at the half-Z position). The controller can configure the position indicators 270-275 to indicate that the transducer 131 is not at the predetermined position along the Z-axis by controlling the position indicators 270-275 to be in a second displayed state different from the first displayed state.

In the examples in which the position indicators 270-275 are lights (e.g., light emitting diodes (LEDs), incandescent lamps, halogen lamps, neon lamps, and so on), the first displayed state corresponds to a first color and the second displayed state corresponds to a second color different from the first color. In further examples in which the position indicators 270-275 are lights, the first display state corresponds to the position indicators 270-275 being switched on and the second displayed state corresponds to the position indicators 270-275 being switched off. In additional examples in which the position indicators 270-275 are lights, the first display state corresponds to the position indicators 270-275 being switched off and the second displayed state corresponds to the position indicators 270-275 being switched on.

As shown, the position indicator 270 is disposed on the front surface 212. The position indicator 271 is disposed on the top surface 216. The position indicator 272 is disposed on the chamfered surface 210. The position indicator 273 is disposed on the side surface 214. The position indicator 274 is disposed on a side surface 219. The position indicator 275 is disposed on the back surface 218. While one of the position indicators 270-275 are shown on each of the surfaces 210, 212, 214, 216, 218, and 219, any number of position indicators can be disposed on any or all of the surfaces 210, 212, 214, 216, 218, and 219. By disposing the position indicators 270-275 on different surfaces of the device housing 200, the operator can observe the position indicators 270-275 from anywhere relative to the device housing 200.

In some examples, the position indicators can be organized as a line or cluster of indicators. For example, a line or cluster of separate position indicators (e.g., lights) can be dispensed over two or more of the surfaces 210, 212, 214, 216, 218, and 219, forming a continuous position indicator over multiple surfaces.

While the position indicators 270-275 shown are lights, other visual cues such as one or more electronic displays can likewise be operatively coupled to the controller to indicate whether the transducer 131 is positioned at the predetermined position (the half-Z position or within the predetermined range centered at the half-Z position). For example, the controller can configure the electronic displays to indicate that the transducer 131 is at the predetermined position along the Z-axis by controlling the electronic displays to display a first display. The controller can configure the electronic displays to indicate that the transducer 131 is not at the predetermined position along the Z-axis by controlling the electronic displays to display a second display distinct from the first display. The first and second display can be different words, different patterns, different graphics, different colors, and so on.

Audio cues such as sound outputted by one or more speakers can likewise be operatively coupled to the controller to indicate whether the transducer 131 is positioned at the predetermined position (the half-Z position or within the predetermined range centered at the half-Z position). For example, the controller can configure the speakers to indicate that the transducer 131 is at the predetermined position along the Z-axis by controlling the speakers to output a first sound. The controller can configure the speakers to indicate that the transducer 131 is not at the predetermined position along the Z-axis by controlling the speakers to output a second sound distinct from the first sound. The first and second sounds can be sounds with one or more of different lengths, different periodicities, different frequencies, different pitches, and so on.

Figure 6A:
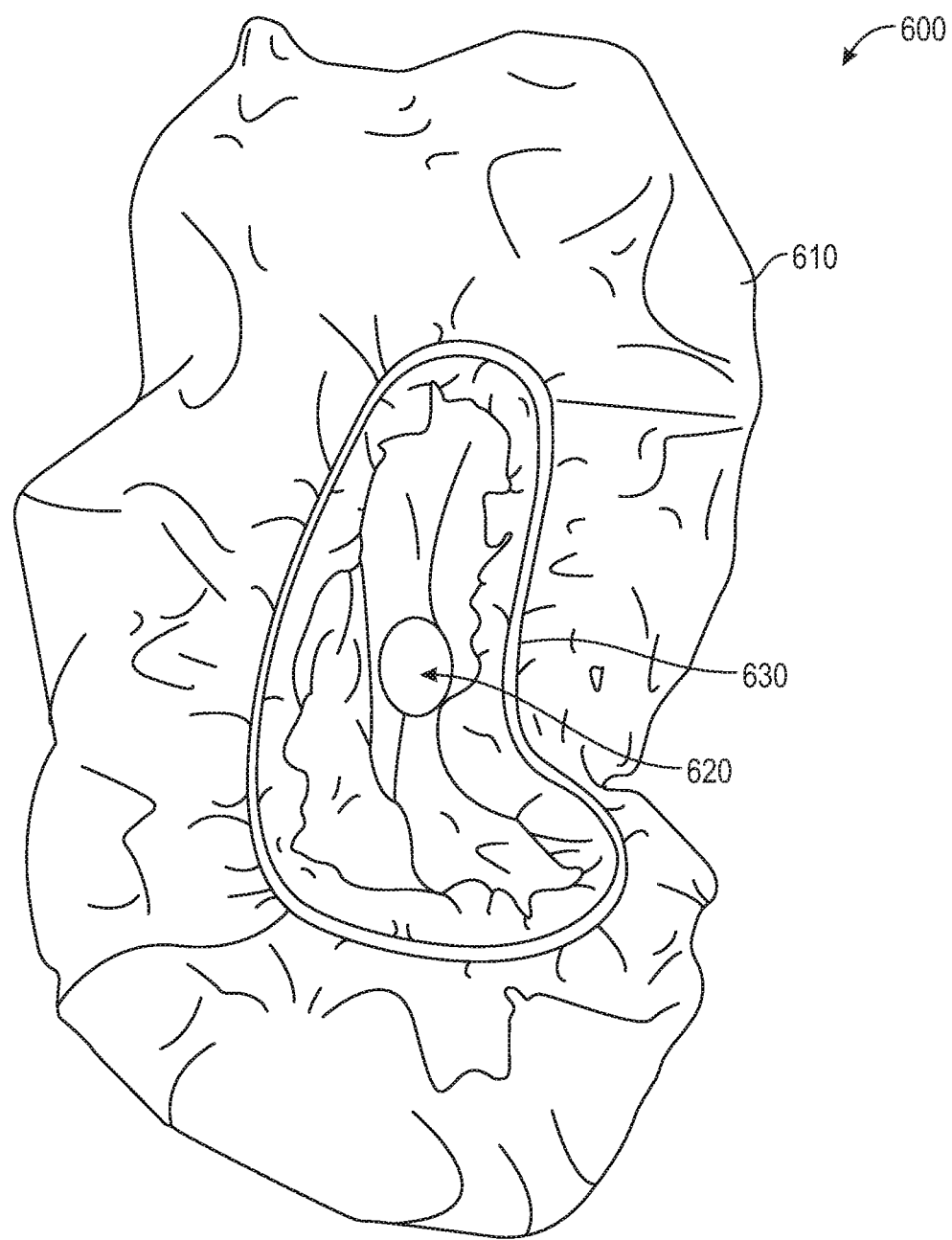
FIG. 6A illustrates a front view of an enclosure according to various arrangements.
Figure 6B:
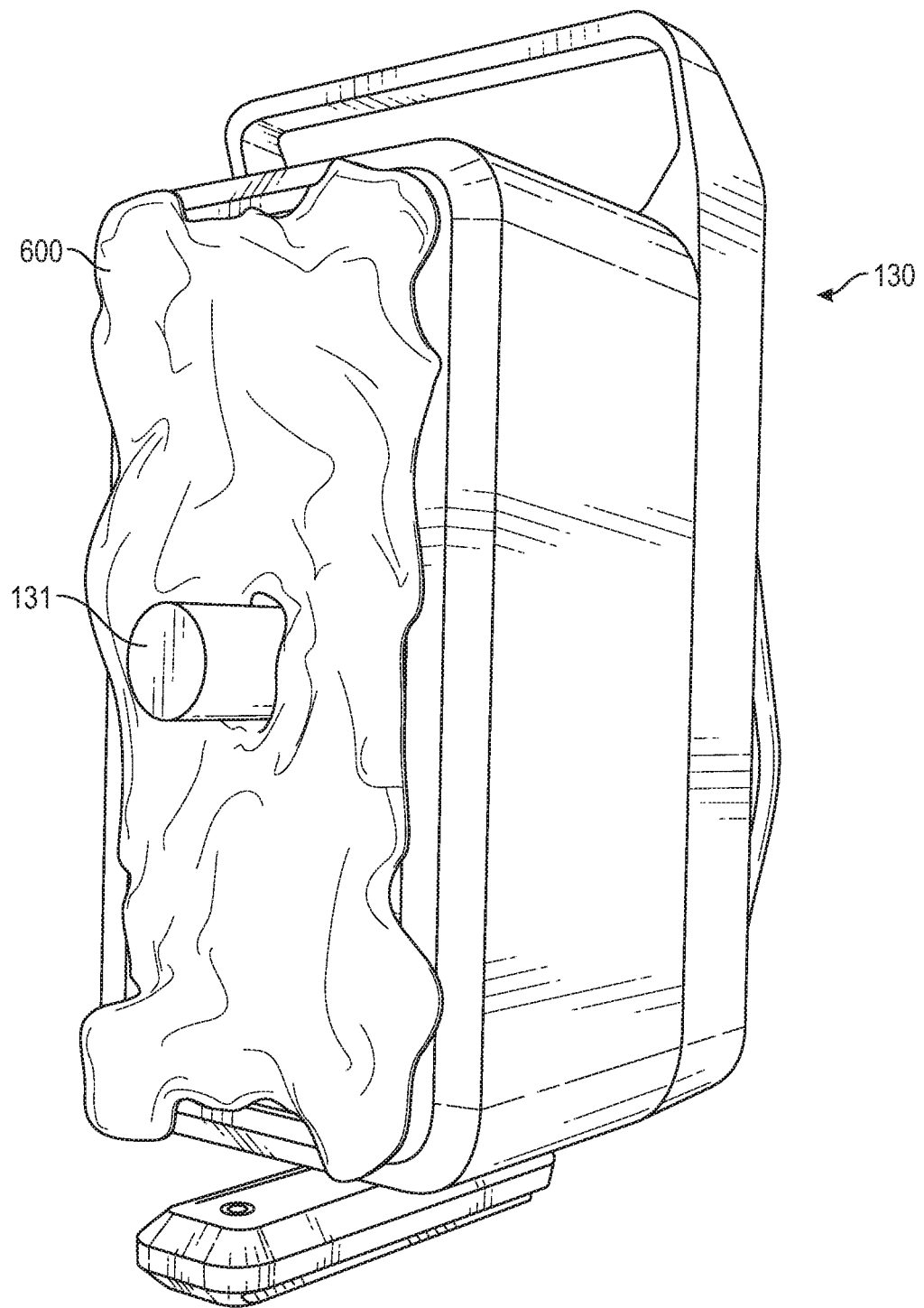
FIG. 6B illustrates the enclosure of FIG. 6A being deployed on the device shown in FIGS. 1-2I according to various arrangements.

During the operation of the probe, particles (e.g., hair) and liquid (e.g., blood and gel) may fall into the cavity 202—a hazard to electronic and mechanical components (e.g., the robotics) of the device 130 that are exposed by the cavity 202. FIG. 6A illustrates a front view of an enclosure 600 according to various arrangements. FIG. 6B illustrates the enclosure 600 of FIG. 6A being deployed on the device 130 shown in FIGS. 1-2I according to various arrangements. Referring to FIGS. 1-6B, the enclosure 600 is configured to seal or otherwise enclose a portion (e.g., the cavity 202) of the device housing 200 to prevent particles (e.g., hair) and/or liquid (e.g., blood and gel) from entering into the cavity 202, thus improving performance and longevity of the device 130.

In some arrangements, the enclosure 600 includes an enclosure body 610. The enclosure body 610 is configured to cover the cavity 202 when the enclosure 600 is attached, fastened, or otherwise coupled to the device housing 200 (e.g., via anchors 240-243). That is, the enclosure 600 is configured to be removably attached to the anchors 240-243 in the manner described. The enclosure body 610 is made of a material that provides ingress protection against liquid (e.g., blood, sweater, and water) and particles (e.g., dust and hair) for the cavity 202. In some arrangements, the enclosure body 610 is made of an elastic material. Furthermore, in some arrangements, the enclosure body 610 is made of a biocompatible material suitable for contacting a human body (e.g., the head of the subject). Therefore, in considering ingress protection, elasticity, and biocompatibility, the enclosure body 610 can be made from a material such as but not limited to, polyethylene (PE), polypropylene (PE), polycarbonate (PC), polyurethane (PU), polyetherimide (PEI), PVC, and polyether ether ketone (PEEK).

The enclosure 600 (e.g., the enclosure body 610) includes a hole 620. The hole 620 is configured to be operatively engaged with the transducer 131, exposing a portion of the transducer 131. For example, the portion of the transducer 131 that is exposed can include the first end that has the concave surface configured to be adjacent to or contact the scanning surface on the head. The transducer 131 can be inserted through the hole 620 to expose the portion of the transducer 131 that is not covered by the enclosure body 610.

In some arrangements, the hole 620 forms a seal around the transducer 131 when the enclosure 600 is attached, fastened, or otherwise coupled to the anchors 240-243. In one example, dimensions (e.g., the radius) of the hole 620 are smaller than corresponding dimensions (e.g., the radius) of the transducer 131. A portion of the enclosure body 610 surrounding the hole 620 forms the seal around the transducer 131 by providing a friction fit with the transducer 131 to prevent liquid and particles from entering into the cavity 202. The friction fit is created as the transducer 131 is inserted through the hole 620, causing the portion of the enclosure body 610 surrounding the hole 620 to stretch to form the seal due to differences of the dimensions of the hole 620 and the corresponding dimensions of the transducer 131.

In some arrangements, when the enclosure 600 is attached, fastened, or otherwise coupled to the anchors 240-243, the portion surrounding and around the hole 620 corresponds to extra material of the enclosure body 610. The extra material forms a pocket-like volume to allow the portion surrounding and around the hole 620 to move freely with the transducer 131 when the enclosure 600 is attached, fastened, or otherwise coupled to the anchors 240-243. Particularly, the extra material allows the transducer 131 to be moved to anywhere within the workspace of the transducer 131 without causing strain or tear in the enclosure body 610.

The enclosure body 610 forms an opening around which a fastening mechanism 630 is provided for attaching, fastening, or otherwise coupling the enclosure body 610 to the anchors 240-243 to allow easy installation and removal of the enclosure 600 and to provide secure placement of the enclosure 600 while on the device 130 and while the device 130 is operating. Although the fastening mechanism 630 is shown to be an elastic band configured to be expanded and tighten around the anchors 240-243 once the enclosure 600 is positioned, other examples of the fastening mechanism 630 include, but are not limited to, Velcro®, adhesive strips, adhesives, buttons, zippers, clamps, and strings.

Further disclosure regarding the enclosure 600 that can be used in conjunction with the headset system 100 described herein can be found in non-provisional patent application Ser. No. 15/952,791, titled ENCLOSURE FOR DEVICE INCLUDING PROBE, and filed on Apr. 13, 2018, which is incorporated herein by reference in its entirety.

The anchors 240-243 are configured to anchor the enclosure 600 configured to enclose at least a portion (e.g., the cavity 202) of the device 130. As shown, the configuration (e.g., positions, sizes, shape, and so on) of the anchors 240-243 defines the shape of the enclosure 600 when the enclosure 600 (e.g., the fastening mechanism 630) engages the anchors 240-243. As such, the anchors 240-243 can be positioned at strategic locations on the device housing 200 such that the enclosure 600 may have a shape that corresponds to (e.g., have the same shape as) or at least approximate the shape of the cavity 202 when the enclosure 600 (e.g., the fastening mechanism 630) engages the anchors 240-243.

As shown, the anchors 240-243 are disposed on an edge portion (e.g., a border) that defines the cavity 202 on the front surface 212. The edge portion includes an interior surface facing an interior of the device housing 200 (e.g., facing the robotics, the controller, and so on). The interior surface is configured to face away from the subject when the transducer 131 collects the physiological data of the subject, when the subject is supported by the support structure 110. In some examples, the anchors 240-243 are attached, fixed, or otherwise coupled to the interior surface of the edge portion. In that regard, at least a portion of each of the anchors 240-243 is disposed within the cavity 202 as shown. In other examples, the edge portion includes an exterior surface facing away from the interior of the device housing 200, and the anchors 240-243 are attached, fixed, or otherwise coupled to the exterior surface of the edge portion. The exterior surface is configured to face the subject when the transducer 131 collects the physiological data of the subject, when the subject is supported by the support structure 110. In further examples, the anchors 240-243 are attached to the device housing 200 (e.g., the front surface 212) on both the interior surface and the exterior surface.

As shown, the anchors 240-243 are disposed around the cavity 202 on the edge portion, where the cavity 202 aligns with (e.g., corresponds to) the XY-plane of the workspace of the transducer 131 as described. To ensure that the enclosure body 610 takes an appropriate form (e.g., a rectangle) to as to cover the cavity 202 when the enclosure 600 is attached, fastened, or otherwise coupled to the anchors 240-243, the anchors 240-243 are disposed on the four corners of the cavity 202. To ensure that the enclosure body 610 to take other forms (e.g., a triangle, a square, a circle, an oval, a hexagon, and so on) corresponding to a cavity of another shape, the anchors can be positioned differently on the edge portion. In an example in which a cavity has a square shape, an anchor is disposed on each of the four corners of the cavity. In an example in which a cavity has a triangle shape, an anchor is disposed on each of the three vertices of the cavity. In an example in which a cavity has a circle or oval shape, multiple (e.g., six or more, even or more, eight or more, nine or more, or ten or more) anchors are disposed around the edge portion of the cavity. In that regard, the number and locations of the anchors depend on the shape of the cavity.

The anchors 240-243 being disposed on the edge portion allows the disposable body 610 (when the enclosure 600 is attached, fastened, or otherwise coupled to the anchors 240-243) to not intrude on the FOV 440 of the camera 105. As such, the anchors 240-243 are not provided on the chamfered surface 210 and are restricted to the front surface 212. The anchors 243 and 242 proximal to the chamfered surface 210 are spaced apart from the chamfered surface 210 by a sufficient distance such that the enclosure 600 is not in the FOV 440 of the camera 105 when the enclosure 600 is attached, fastened, or otherwise coupled to the anchors 240-243.

As shown, each of the anchors 240-243 is or otherwise includes a hook. As shown, each of the anchors 240-243 has a first portion that extends from the edge portion and a second portion connected to the first portion, where the second portion bends away from the transducer 131 or the cavity 202. As shown, the home or initial position of the transducer 131 is in the center of the anchors 240-243. The second portions of the anchors 240-243 bend away from the home or initial position of the transducer 131. The first portion may be perpendicular or oblique to the front surface 212. The second portion may be parallel or oblique to the front surface 212. The first and second portions are configured (sized and shaped) to engage and retain the fastening mechanism 630 (the elastic band) when the fastening mechanism 630 is placed over the anchors 240-243. In some examples, the fastening mechanism 630 includes suitable adhesive used to attach the enclosure body 610 to the anchors 240-243.

As shown, the second portion of each of the anchors 240-243 has a quarter-circle shape. The quarter-circle allows a large surface area to retain the fastening mechanism 630 (securing the fastening mechanism 630 between the first and second portions) while having a smooth edge of the quarter-circle to contact the enclosure body 610 without any risk of the smooth edge piercing the enclosure body 610. In other examples, the second portion may have another suitable shape such as but not limited to, a half circle, a circle, an oval, a square, a rectangle, and so on.

In other arrangements, instead of the hook-like anchors 240-243, a raised edge around the edge portion on the front surface 212 with a groove facing away from the cavity 202 and the transducer 131 are used to retain the fastening mechanism 630.

In some arrangements, the headset system 100 as described herein is used in conjunction with other diagnostic ultrasound procedures, such as, but not limited to, needle guidance, intravascular ultrasound (e.g., examination of vessels, blood flow characteristics, clot identification, emboli monitoring, and so on), echocardiograms, abdominal sonography (e.g., imaging of the pancreas, aorta, inferior vena cava, liver, gall bladder, bile ducts, kidneys, spleen, appendix, rectal area, and so on), gynecologic ultrasonography (e.g., examination of pelvic organs such as uterus, ovaries, Fallopian tubes, and so on), obstetrical sonography, otolaryngological sonography (e.g., imaging of the thyroid (such as for tumors and lesions), lymph nodes, salivary glands, and so on), neonatal sonography (e.g., assessment of intracerebral structural abnormalities through soft spots of a skull of an infant, bleeds, ventriculomegaly, hyrdrocephalus, anoxic insults, and so on), ophthamological procedures (e.g., A-scan ultrasound biometry, B-scan ultrasonography, and so on), pulmonological uses (e.g., endobronchial ultrasound (EBUS)), urological procedures (e.g., determination of an amount of fluid retained in a subject's bladder, imaging of pelvic organs (such as uterus, ovaries, urinary bladder, prostate, and testicles), and detection of kidney stones), scrotal sonography (e.g., to evaluate testicular pain, identify solid masses, and so on), musculoskeletal procedures (e.g., examination of tendons, muscles, nerves, ligaments, soft tissue masses, bone surfaces, and so on), bone fracture sonography, testing for myopathic disease, estimating lean body mass, proxy measures of muscle quality (e.g., tissue composition), nephrological procedures (e.g., renal ultrasonography), and so on.

In some arrangements, the headset system 100 as described herein is used in conjunction with therapeutic ultrasound procedures, such as, but not limited to, high-intensity focused ultrasound (HIFU), focused ultrasound surgery (FUS), Magnetic resonance-guided focused ultrasound (MRgFUS), lithotripsy (e.g., breaking up kidney stones, bezoars, gall stones, and so on), targeted ultrasound drug delivery, trans-dermal ultrasound drug delivery, ultrasound hemostasis, cancer therapy, ultrasound-assisted thrombolysis, dental hygiene (e.g., cleaning teeth), phacoemulsification, ablation (e.g., of tumors or other tissue), acoustic targeted drug delivery (ATDD), trigger release of drugs (e.g., anti-cancer drugs), ultrasound-guided treatments (sclerotherapy, endovenous laser treatment, liposuction, and so on), and so on. In some arrangements, ultrasound is used for physical therapy applications, including, but not limited to, stimulating tissue beneath the skin's surface (e.g., by using very high frequency sound waves, such as, as an example, between about 800,000 Hz and 2,000,000 Hz), treating musculoskeletal ailments with ultrasound exposure (e.g., ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion), and so on.

The above used terms, including "held fast," "mount," "attached," "coupled," "affixed," "connected," "secured," and so on are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element. As used herein, two mechanical components that are "configured" to be coupled in any suitable manner (e.g., to engage, to fit, to support, to receive, and so on) with respect to one another are sized and shaped (e.g., sized and shaped to engage, sized and shaped to fit, sized and shaped to support, sized and shaped to receive, and so on) to be coupled accordingly.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the examples disclosed herein may be implemented or performed with a general purpose processor, a DSP, an ASIC, an FPGA or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

What is claimed is:

1. A headset system, comprising:
   a transducer configured to collect physiological data of a subject;
   a device housing configured to support the transducer;
   an insert portion disposed on the device housing;
   a support structure comprising a baseplate and a receiving portion, wherein the receiving portion has a length that extends in a direction that is oblique with respect to the baseplate when the baseplate is placed on a surface; and
   a head cradle supported by the baseplate, wherein the insert portion is sized and shaped to engage the receiving portion to removably attach the device housing to the baseplate, wherein the transducer is configured to move relative to the device housing while the insert portion engages the receiving portion in the same direction that is oblique with respect to the baseplate.

2. The headset system of claim 1, wherein the receiving portion extends in an oblique direction from the baseplate.

3. The headset system of claim 1, wherein
   the receiving portion comprises a body and a receptacle; and
   the receptacle forms an aperture configured to receive the insert portion.

4. The headset system of claim 3, wherein
   the aperture has an inner surface comprising slots;
   the insertion portion comprises a rail having teeth; and
   the teeth are configured to engage the slots when the insertion portion is engaged with the receiving portion.

5. The headset system of claim 3, wherein
   the insert portion comprises an extension having a top surface and a bottom surface;
   the bottom surface faces away from the device housing; and
   the rail is disposed on the bottom surface.

6. The headset system of claim 3, wherein the body extends in an oblique direction from the baseplate.

7. The headset system of claim 3, wherein
   the body extends from the baseplate in a first direction;
   the receptacle extends in a second direction; and
   the first direction traverses the second direction.

8. The headset system of claim 1, wherein at least a portion of the insert portion has a flat shape.

9. The headset system of claim 8, wherein the device housing is configured to stand upright on a surface via the portion of the insert portion having the flat shape.

10. The headset system of claim 1, wherein
the transducer extends from the device housing in a first direction;
the insertion portion extends in a second direction; and
the first direction and the second direction are parallel.

11. The headset system of claim 1, further comprising an actuator configured to lock the insert portion in a position relative to the receiving portion when at least a part of the insert portion is inserted into the receiving portion.

12. The headset system of claim 11, wherein the actuator comprises a latch disposed on the device housing.

13. The headset system of claim 11, wherein
the insertion portion comprises a rail having teeth; and
the actuator is configured to lock the insert portion in the position relative to the receiving portion by controlling a position of the rail.

14. The headset system of claim 13, wherein the actuator is configured to control the position of the rail via a lever mechanism connecting the actuator with the rail.

15. The headset system of claim 13, wherein the rail faces an opening slit of the receiving portion.

16. The headset system of claim 11, wherein
the transducer extends from the device housing in a first direction;
the actuator is arranged on a surface of the device housing that faces a second direction; and
the first direction and the second direction are opposite.

17. The headset system of claim 11, wherein
the device housing comprises a first portion and a second portion separate from the first portion;
the first portion is configured to support the transducer; and
the actuator is disposed on the second portion.

18. The headset system of claim 17, wherein the insert portion is disposed on the first portion.

19. The headset system of claim 17, wherein the insert portion is disposed on the second portion.

20. The headset system of claim 1, wherein at least a portion of the insert portion is detachably mounted to the device housing.

21. A headset system, comprising:
a transducer configured to collect physiological data of a subject;
a device housing configured to support the transducer, the transducer is disposed on a front side of the device housing;
an insert portion disposed on the device housing;
a support structuring comprising a baseplate and a receiving portion, wherein the receiving portion has a length that extends in an oblique direction from the baseplate;
a head cradle supported by the baseplate, wherein the insert portion is sized and shaped to engage the receiving portion to removably attach the device housing to the baseplate, wherein the transducer is configured to move relative to the device housing while the insert portion engages the receiving portion in the same direction that is oblique with respect to the baseplate; and
an actuator disposed on a back side of the device housing, wherein the front side and the back side are opposite sides of the device housing.

* * * * *